United States Patent
Yao et al.

(10) Patent No.: US 8,497,121 B2
(45) Date of Patent: Jul. 30, 2013

(54) METHOD OF OBTAINING VIABLE SMALL TISSUE PARTICLES AND USE FOR TISSUE REPAIR

(75) Inventors: Jian Q. Yao, Shanghai (CN); Victor Zaporojan, Richardson, TX (US)

(73) Assignee: Zimmer Orthobiologics, Inc., Austin, TX (US)

( * ) Notice: Subject to any disclaimer, the term of this patent is extended or adjusted under 35 U.S.C. 154(b) by 0 days.

(21) Appl. No.: 13/428,873

(22) Filed: Mar. 23, 2012

(65) Prior Publication Data
US 2012/0183586 A1 Jul. 19, 2012

Related U.S. Application Data

(63) Continuation of application No. 11/613,250, filed on Dec. 20, 2006, now Pat. No. 8,163,549.

(51) Int. Cl.
*C12N 5/00* (2006.01)
(52) U.S. Cl.
USPC .......................................... 435/325; 424/426
(58) Field of Classification Search
None
See application file for complete search history.

(56) References Cited

U.S. PATENT DOCUMENTS

| | | | |
|---|---|---|---|
| 1,347,622 A | 7/1920 | Deininger |
| 2,533,004 A | 12/1950 | Ferry et al. |
| 2,621,145 A | 12/1952 | Sano |
| 3,400,199 A | 9/1968 | Balassa |
| 3,474,146 A | 10/1969 | Baker et al. |
| 3,476,855 A | 11/1969 | Balassa |
| 3,478,146 A | 11/1969 | Balassa |
| 3,772,432 A | 11/1973 | Balassal |
| RE28,093 E | 7/1974 | Balassa |
| 3,966,908 A | 6/1976 | Balassal |
| 4,440,680 A | 4/1984 | Cioca |
| 4,453,939 A | 6/1984 | Zimmerman et al. |
| 4,479,271 A | 10/1984 | Bolesky et al. |
| 4,522,096 A | 6/1985 | Niven, Jr. |
| 4,566,138 A | 1/1986 | Lewis et al. |
| 4,587,766 A | 5/1986 | Miyatake et al. |
| 4,609,551 A | 9/1986 | Caplan et al. |
| 4,627,879 A | 12/1986 | Rose et al. |
| 4,640,834 A | 2/1987 | Eibl et al. |
| 4,641,651 A | 2/1987 | Card |
| 4,642,120 A | 2/1987 | Nevo et al. |
| 4,656,137 A | 4/1987 | Balassa |
| 4,660,755 A | 4/1987 | Farling |
| 4,714,457 A | 12/1987 | Alterbaum |
| 4,773,418 A | 9/1988 | Hettich |
| 4,818,633 A | 4/1989 | Dinwoodie et al. |
| 4,846,835 A | 7/1989 | Grande |
| 4,851,354 A | 7/1989 | Winston et al. |
| 4,863,474 A | 9/1989 | Brown et al. |
| 4,863,475 A | 9/1989 | Andersen et al. |
| 4,904,259 A | 2/1990 | Itay |
| 4,911,720 A | 3/1990 | Collier |
| 4,928,603 A | 5/1990 | Rose et al. |
| 4,952,403 A | 8/1990 | Vallee et al. |
| 4,963,489 A | 10/1990 | Naughton et al. |
| 4,997,444 A | 3/1991 | Farling |
| 4,997,445 A | 3/1991 | Hodorek |
| 5,002,071 A | 3/1991 | Harrell |
| 5,002,582 A | 3/1991 | Guire et al. |
| 5,013,324 A | 5/1991 | Zolman et al. |
| 5,018,285 A | 5/1991 | Zolman et al. |
| 5,030,215 A | 7/1991 | Morse et al. |
| 5,032,508 A | 7/1991 | Naughton et al. |
| 5,041,138 A | 8/1991 | Vacanti et al. |
| 5,053,050 A | 10/1991 | Itay |
| 5,067,963 A | 11/1991 | Khouri et al. |
| 5,067,964 A | 11/1991 | Richmond et al. |
| 5,069,881 A | 12/1991 | Clarkin |
| 5,080,674 A | 1/1992 | Jacobs et al. |
| 5,092,887 A | 3/1992 | Gendler |
| 5,130,418 A | 7/1992 | Thompson |
| 5,139,527 A | 8/1992 | Redl et al. |
| 5,189,148 A | 2/1993 | Akiyama et al. |
| 5,198,308 A | 3/1993 | Shetty et al. |
| 5,206,023 A | 4/1993 | Hunziker |
| 5,217,954 A | 6/1993 | Foster et al. |
| 5,219,363 A | 6/1993 | Crowninshield et al. |
| 5,226,914 A | 7/1993 | Caplan et al. |

(Continued)

FOREIGN PATENT DOCUMENTS

| AU | 199871003 B2 | 10/1998 |
|---|---|---|
| AU | 2006282754 A2 | 3/2007 |

(Continued)

OTHER PUBLICATIONS

Huang et al., Tissue Engineering, 2002, vol. 8, No. 3, p. 469-481.*
Kim et al., OsteoArthritis and Cartilage, 2003, vol. 11, p. 653-664.*
U.S. Appl. No. 10/374,777, 1.132 Declaration of Julia Hwang filed Jan. 5, 2009, 3 pgs.
U.S. Appl. No. 10/374,772, Response filed Jan. 6, 2009 to Non-Final Office Action mailed Sep. 2, 2008, 5 pgs.

(Continued)

*Primary Examiner* — Kade Ariani
(74) *Attorney, Agent, or Firm* — Schwegman, Lundberg & Woessner P.A.

(57) ABSTRACT

The invention provides a composition including isolated small living tissue particles, a method of making the tissue particles, and a method of using the composition to ameliorate a tissue defect. The tissue particles are composed of cells and their associated extracellular molecules and are sized, in certain embodiments, to be smaller than about 1 mm. Another aspect of the inventive tissue particles is the large percentage of viable cells. In certain embodiments, the tissue particles are made from cartilage and the composition may also contain additives such as adhesives, solutions, and bioactive agents.

21 Claims, 4 Drawing Sheets

U.S. PATENT DOCUMENTS

| | | |
|---|---|---|
| 5,236,457 A | 8/1993 | Devanathan |
| 5,254,471 A | 10/1993 | Mori et al. |
| 5,269,785 A | 12/1993 | Bonutti |
| 5,270,300 A | 12/1993 | Hunziker |
| 5,281,422 A | 1/1994 | Badylak et al. |
| 5,282,861 A | 2/1994 | Kaplan |
| 5,290,552 A | 3/1994 | Sierra et al. |
| 5,290,558 A | 3/1994 | O'Leary et al. |
| 5,312,417 A | 5/1994 | Wilk |
| 5,323,954 A | 6/1994 | Shetty et al. |
| 5,326,357 A | 7/1994 | Kandel |
| 5,345,927 A | 9/1994 | Bonutti |
| 5,356,629 A | 10/1994 | Sander et al. |
| 5,368,858 A | 11/1994 | Hunziker |
| 5,372,821 A | 12/1994 | Badylak et al. |
| 5,387,243 A | 2/1995 | Devanathan |
| 5,403,317 A | 4/1995 | Bonutti |
| 5,405,607 A | 4/1995 | Epstein |
| 5,410,016 A | 4/1995 | Hubbell et al. |
| 5,443,454 A | 8/1995 | Tanabe et al. |
| 5,443,510 A | 8/1995 | Shetty et al. |
| 5,443,512 A | 8/1995 | Parr et al. |
| 5,445,833 A | 8/1995 | Badylak et al. |
| 5,456,723 A | 10/1995 | Steinemann et al. |
| 5,456,828 A | 10/1995 | Tersi et al. |
| 5,461,953 A | 10/1995 | Mccormick |
| 5,475,052 A | 12/1995 | Rhee et al. |
| 5,482,929 A | 1/1996 | Fukunaga et al. |
| 5,496,375 A | 3/1996 | Sisk et al. |
| 5,504,300 A | 4/1996 | Devanathan et al. |
| 5,510,396 A | 4/1996 | Prewett et al. |
| 5,514,536 A | 5/1996 | Taylor |
| 5,516,532 A | 5/1996 | Atala et al. |
| 5,516,533 A | 5/1996 | Badylak et al. |
| 5,535,810 A | 7/1996 | Compton et al. |
| 5,545,222 A | 8/1996 | Bonutti |
| 5,549,704 A | 8/1996 | Sutter |
| 5,549,904 A | 8/1996 | Juergensen et al. |
| 5,554,389 A | 9/1996 | Badylak et al. |
| 5,556,429 A | 9/1996 | Felt |
| 5,565,519 A | 10/1996 | Rhee et al. |
| 5,571,187 A | 11/1996 | Devanathan |
| 5,577,517 A | 11/1996 | Bonutti |
| 5,578,492 A | 11/1996 | Fedun |
| 5,585,007 A | 12/1996 | Antanavich et al. |
| 5,605,887 A | 2/1997 | Pines et al. |
| 5,612,028 A | 3/1997 | Sackier et al. |
| 5,618,925 A | 4/1997 | Dupont et al. |
| 5,624,463 A | 4/1997 | Stone et al. |
| 5,639,280 A | 6/1997 | Warner et al. |
| 5,643,192 A | 7/1997 | Hirsh |
| 5,650,494 A | 7/1997 | Cerletti et al. |
| 5,654,166 A | 8/1997 | Kurth |
| 5,655,546 A | 8/1997 | Halpern |
| 5,656,587 A | 8/1997 | Sporn et al. |
| 5,662,710 A | 9/1997 | Bonutti |
| 5,669,544 A | 9/1997 | Schulze et al. |
| 5,672,284 A | 9/1997 | Devanathan et al. |
| 5,673,840 A | 10/1997 | Schulze et al. |
| 5,673,841 A | 10/1997 | Schulze et al. |
| 5,680,982 A | 10/1997 | Schulze et al. |
| 5,681,353 A | 10/1997 | Li et al. |
| 5,692,668 A | 12/1997 | Schulze et al. |
| 5,694,951 A | 12/1997 | Bonutti |
| 5,695,998 A | 12/1997 | Badylak et al. |
| 5,709,854 A | 1/1998 | Griffith-Cima et al. |
| 5,713,374 A | 2/1998 | Pachence et al. |
| 5,714,371 A | 2/1998 | Ramanathan et al. |
| 5,723,010 A | 3/1998 | Yui et al. |
| 5,723,011 A | 3/1998 | Devanathan et al. |
| 5,723,331 A | 3/1998 | Tubo et al. |
| 5,734,959 A | 3/1998 | Krebs et al. |
| 5,735,875 A | 4/1998 | Bonutti et al. |
| 5,736,132 A | 4/1998 | Juergensen et al. |
| 5,736,396 A | 4/1998 | Bruder et al. |
| 5,749,968 A | 5/1998 | Melanson et al. |
| 5,753,485 A | 5/1998 | Dwulet et al. |
| 5,755,791 A | 5/1998 | Whitson et al. |
| 5,769,899 A | 6/1998 | Schwartz et al. |
| 5,770,194 A | 6/1998 | Edwardson et al. |
| 5,782,835 A | 7/1998 | Hart et al. |
| 5,782,915 A | 7/1998 | Stone |
| 5,786,217 A | 7/1998 | Tubo et al. |
| 5,788,662 A | 8/1998 | Antanavich et al. |
| 5,795,571 A | 8/1998 | Cederholm-Williams et al. |
| 5,795,780 A | 8/1998 | Cederholm-Williams et al. |
| 5,811,094 A | 9/1998 | Caplan et al. |
| 5,824,093 A | 10/1998 | Ray et al. |
| 5,826,776 A | 10/1998 | Schulze et al. |
| 5,827,217 A | 10/1998 | Silver et al. |
| 5,830,741 A | 11/1998 | Dwulet et al. |
| 5,842,477 A | 12/1998 | Naughton et al. |
| 5,853,746 A | 12/1998 | Hunziker |
| 5,853,976 A | 12/1998 | Hesse et al. |
| 5,864,016 A | 1/1999 | Eibl et al. |
| 5,866,415 A | 2/1999 | Villeneuve |
| 5,866,630 A | 2/1999 | Mitra et al. |
| 5,876,208 A | 3/1999 | Mitra et al. |
| 5,876,451 A | 3/1999 | Yui et al. |
| 5,876,452 A | 3/1999 | Athanasiou et al. |
| 5,879,398 A | 3/1999 | Swarts et al. |
| 5,888,219 A | 3/1999 | Bonutti |
| 5,888,491 A | 3/1999 | Mitra et al. |
| 5,890,898 A | 4/1999 | Wada et al. |
| 5,891,455 A | 4/1999 | Sittinger et al. |
| 5,899,936 A | 5/1999 | Goldstein |
| 5,902,741 A | 5/1999 | Purchio et al. |
| 5,919,702 A | 7/1999 | Purchio et al. |
| 5,921,987 A | 7/1999 | Stone |
| 5,922,027 A | 7/1999 | Stone |
| 5,922,846 A | 7/1999 | Cerletti et al. |
| 5,926,685 A | 7/1999 | Krebs et al. |
| 5,928,945 A | 7/1999 | Seliktar et al. |
| 5,935,131 A | 8/1999 | Bonutti |
| 5,944,754 A | 8/1999 | Vacanti |
| 5,944,755 A | 8/1999 | Stone |
| 5,948,384 A | 9/1999 | Filler |
| 5,952,215 A | 9/1999 | Dwulet et al. |
| 5,962,405 A | 10/1999 | Seelich |
| 5,964,752 A | 10/1999 | Stone |
| 5,964,805 A | 10/1999 | Stone |
| 5,968,556 A | 10/1999 | Atala et al. |
| 5,985,315 A | 11/1999 | Patat et al. |
| 5,989,269 A | 11/1999 | Vibe-hansen et al. |
| 5,989,888 A | 11/1999 | Dwulet et al. |
| 6,022,361 A | 2/2000 | Epstein et al. |
| 6,025,334 A | 2/2000 | Dupont et al. |
| 6,041,723 A | 3/2000 | Peterson |
| 6,045,990 A | 4/2000 | Baust et al. |
| 6,048,966 A | 4/2000 | Edwardson et al. |
| 6,051,249 A | 4/2000 | Samuelsen |
| 6,059,198 A | 5/2000 | Moroi et al. |
| 6,060,053 A | 5/2000 | Atala |
| 6,077,989 A | 6/2000 | Kandel et al. |
| 6,080,194 A | 6/2000 | Pachence et al. |
| 6,080,579 A | 6/2000 | Hanley et al. |
| 6,083,383 A | 7/2000 | Huang et al. |
| 6,087,553 A | 7/2000 | Cohen et al. |
| 6,107,085 A | 8/2000 | Coughlin et al. |
| 6,110,209 A | 8/2000 | Stone |
| 6,110,210 A | 8/2000 | Norton et al. |
| 6,110,212 A | 8/2000 | Gregory |
| 6,110,482 A | 8/2000 | Khouri et al. |
| 6,120,514 A | 9/2000 | Vibe-hansen et al. |
| 6,129,761 A | 10/2000 | Hubbell |
| 6,132,465 A | 10/2000 | Ray et al. |
| 6,132,472 A | 10/2000 | Bonutti |
| 6,140,123 A | 10/2000 | Demetriou et al. |
| 6,140,452 A | 10/2000 | Felt et al. |
| 6,143,214 A | 11/2000 | Barlow |
| 6,150,163 A | 11/2000 | McPherson et al. |
| 6,152,142 A | 11/2000 | Tseng |
| 6,162,241 A | 12/2000 | Coury et al. |
| 6,171,610 B1 | 1/2001 | Vacanti et al. |
| 6,174,313 B1 | 1/2001 | Bonutti |
| 6,179,871 B1 | 1/2001 | Halpern |
| 6,183,737 B1 | 2/2001 | Zaleske et al. |

| Patent | Kind | Date | Inventor |
|---|---|---|---|
| 6,187,329 | B1 | 2/2001 | Agrawal et al. |
| 6,200,330 | B1 | 3/2001 | Benderev et al. |
| 6,203,526 | B1 | 3/2001 | McBeth et al. |
| 6,224,893 | B1 | 5/2001 | Langer et al. |
| 6,235,316 | B1 | 5/2001 | Adkisson |
| 6,242,247 | B1 | 6/2001 | Reiser et al. |
| 6,248,114 | B1 | 6/2001 | Ysebaert |
| 6,264,659 | B1 | 7/2001 | Ross et al. |
| 6,271,320 | B1 | 8/2001 | Keller et al. |
| 6,274,090 | B1 | 8/2001 | Coelho et al. |
| 6,280,993 | B1 | 8/2001 | Yamato et al. |
| 6,294,656 | B1 | 9/2001 | Mittl et al. |
| 6,306,169 | B1 | 10/2001 | Lee et al. |
| 6,306,177 | B1 | 10/2001 | Felt et al. |
| 6,312,668 | B2 | 11/2001 | Mitra et al. |
| 6,322,563 | B1 | 11/2001 | Cummings et al. |
| 6,327,257 | B1 | 12/2001 | Khalifa |
| 6,336,930 | B1 | 1/2002 | Stalcup et al. |
| 6,338,878 | B1 | 1/2002 | Overton et al. |
| 6,358,266 | B1 | 3/2002 | Bonutti |
| 6,361,565 | B1 | 3/2002 | Bonutti |
| 6,368,298 | B1 | 4/2002 | Beretta et al. |
| 6,368,784 | B1 | 4/2002 | Murray |
| 6,370,920 | B1 | 4/2002 | Overton et al. |
| 6,378,527 | B1 | 4/2002 | Hungerford et al. |
| 6,395,327 | B1 | 5/2002 | Shetty |
| 6,417,320 | B1 | 7/2002 | Otto et al. |
| 6,423,063 | B1 | 7/2002 | Bonutti |
| 6,425,704 | B2 | 7/2002 | Voiers et al. |
| 6,436,143 | B1 | 8/2002 | Ross et al. |
| 6,437,018 | B1 | 8/2002 | Gertzman et al. |
| 6,443,988 | B2 | 9/2002 | Felt et al. |
| 6,444,228 | B1 | 9/2002 | Baugh et al. |
| 6,447,514 | B1 | 9/2002 | Stalcup et al. |
| 6,464,713 | B2 | 10/2002 | Bonutti |
| 6,468,289 | B1 | 10/2002 | Bonutti |
| 6,468,527 | B2 | 10/2002 | Austin et al. |
| 6,472,162 | B1 | 10/2002 | Coelho et al. |
| 6,475,764 | B1 | 11/2002 | Burtscher et al. |
| 6,482,235 | B1 | 11/2002 | Lambrecht et al. |
| 6,485,723 | B1 | 11/2002 | Badylak et al. |
| 6,492,163 | B1 | 12/2002 | Yoo et al. |
| 6,497,903 | B1 | 12/2002 | Hennink et al. |
| 6,503,267 | B2 | 1/2003 | Bonutti et al. |
| 6,503,277 | B2 | 1/2003 | Bonutti |
| 6,504,079 | B2 | 1/2003 | Tucker et al. |
| 6,511,958 | B1 | 1/2003 | Atkinson et al. |
| 6,514,514 | B1 | 2/2003 | Atkinson et al. |
| 6,514,522 | B2 | 2/2003 | Domb |
| 6,528,052 | B1 | 3/2003 | Smith et al. |
| 6,533,817 | B1 | 3/2003 | Norton et al. |
| 6,534,084 | B1 | 3/2003 | Vyakarnam et al. |
| 6,534,591 | B2 | 3/2003 | Rhee et al. |
| 6,543,455 | B2 | 4/2003 | Bonutti |
| 6,544,472 | B1 | 4/2003 | Compton et al. |
| 6,551,355 | B1 | 4/2003 | Lewandrowski et al. |
| 6,559,119 | B1 | 5/2003 | Burgess et al. |
| 6,575,982 | B1 | 6/2003 | Bonutti |
| 6,576,265 | B1 | 6/2003 | Spievack |
| 6,579,538 | B1 | 6/2003 | Spievack |
| 6,582,960 | B1 | 6/2003 | Martin et al. |
| 6,592,531 | B2 | 7/2003 | Bonutti |
| 6,596,180 | B2 | 7/2003 | Baugh et al. |
| 6,599,515 | B1 | 7/2003 | Delmotte |
| 6,607,534 | B2 | 8/2003 | Bonutti |
| 6,610,033 | B1 | 8/2003 | Melanson et al. |
| 6,620,169 | B1 | 9/2003 | Peterson et al. |
| 6,626,859 | B2 | 9/2003 | Von Segesser |
| 6,626,945 | B2 | 9/2003 | Simon et al. |
| 6,626,950 | B2 | 9/2003 | Brown et al. |
| 6,630,000 | B1 | 10/2003 | Bonutti |
| 6,632,246 | B1 | 10/2003 | Simon et al. |
| 6,632,648 | B1 | 10/2003 | Kampinga et al. |
| 6,637,437 | B1 | 10/2003 | Hungerford et al. |
| 6,638,309 | B2 | 10/2003 | Bonutti |
| 6,645,316 | B1 | 11/2003 | Brouwer et al. |
| 6,645,764 | B1 | 11/2003 | Adkisson |
| 6,649,168 | B2 | 11/2003 | Arvinte et al. |
| 6,652,532 | B2 | 11/2003 | Bonutti |
| 6,652,872 | B2 | 11/2003 | Nevo et al. |
| 6,652,883 | B2 | 11/2003 | Goupil et al. |
| 6,653,062 | B1 | 11/2003 | DePablo et al. |
| 6,662,805 | B2 | 12/2003 | Frondoza et al. |
| 6,663,616 | B1 | 12/2003 | Roth et al. |
| 6,676,971 | B2 | 1/2004 | Goupil et al. |
| 6,685,987 | B2 | 2/2004 | Shetty |
| 6,697,143 | B2 | 2/2004 | Freeman |
| 6,705,790 | B2 | 3/2004 | Quintero et al. |
| 6,713,772 | B2 | 3/2004 | Goodman et al. |
| 6,719,803 | B2 | 4/2004 | Bonutti |
| 6,719,901 | B2 | 4/2004 | Dolecek et al. |
| 6,730,299 | B1 | 5/2004 | Tayot et al. |
| 6,733,515 | B1 | 5/2004 | Edwards et al. |
| 6,736,853 | B2 | 5/2004 | Bonutti |
| 6,737,072 | B1 | 5/2004 | Angele |
| 6,740,186 | B2 | 5/2004 | Hawkins et al. |
| 6,743,232 | B2 | 6/2004 | Overaker et al. |
| 6,773,458 | B1 | 8/2004 | Brauker et al. |
| 6,773,713 | B2 | 8/2004 | Bonassar et al. |
| 6,776,938 | B2 | 8/2004 | Bonutti |
| 6,797,006 | B2 | 9/2004 | Hodorek |
| 6,800,663 | B2 | 10/2004 | Asgarzadeh et al. |
| 6,818,008 | B1 | 11/2004 | Cates et al. |
| 6,830,762 | B2 | 12/2004 | Baugh et al. |
| 6,833,408 | B2 | 12/2004 | Sehl et al. |
| 6,835,198 | B2 | 12/2004 | Bonutti |
| 6,835,277 | B2 | 12/2004 | Park |
| 6,840,960 | B2 | 1/2005 | Bubb |
| 6,852,330 | B2 | 2/2005 | Bowman et al. |
| 6,860,904 | B2 | 3/2005 | Bonutti |
| 6,884,428 | B2 | 4/2005 | Binette et al. |
| 6,886,568 | B2 | 5/2005 | Frondoza et al. |
| 6,893,466 | B2 | 5/2005 | Trieu |
| 6,905,517 | B2 | 6/2005 | Bonutti |
| 6,919,067 | B2 | 7/2005 | Filler et al. |
| 6,919,172 | B2 | 7/2005 | DePablo et al. |
| 6,921,633 | B2 | 7/2005 | Baust et al. |
| 6,942,880 | B1 | 9/2005 | Dolecek |
| 6,949,252 | B2 | 9/2005 | Mizuno et al. |
| 6,979,307 | B2 | 12/2005 | Beretta et al. |
| 6,990,982 | B1 | 1/2006 | Bonutti |
| 6,991,652 | B2 | 1/2006 | Burg |
| 7,009,039 | B2 | 3/2006 | Yayon et al. |
| 7,045,601 | B2 | 5/2006 | Metzner et al. |
| 7,067,123 | B2 | 6/2006 | Gomes et al. |
| 7,081,125 | B2 | 7/2006 | Edwards et al. |
| 7,083,964 | B2 | 8/2006 | Kurfurst et al. |
| 7,087,227 | B2 | 8/2006 | Adkisson |
| RE39,321 | E | 10/2006 | MacPhee et al. |
| 7,134,437 | B2 | 11/2006 | Bonutti |
| 7,147,471 | B2 | 12/2006 | Frey et al. |
| 7,217,294 | B2 | 5/2007 | Kusanagi et al. |
| 7,235,255 | B2 | 6/2007 | Austin et al. |
| 7,273,756 | B2 | 9/2007 | Adkisson et al. |
| 7,276,235 | B2 | 10/2007 | Metzner et al. |
| 7,276,481 | B2 | 10/2007 | Golembo et al. |
| 7,299,805 | B2 | 11/2007 | Bonutti |
| 7,316,822 | B2 | 1/2008 | Binette et al. |
| 7,375,077 | B2 | 5/2008 | Mao |
| 7,468,192 | B2 | 12/2008 | Mizuno et al. |
| 7,488,348 | B2 | 2/2009 | Truncale et al. |
| 7,537,780 | B2 | 5/2009 | Mizuno et al. |
| 7,720,533 | B2 | 5/2010 | Behravesh et al. |
| 7,824,711 | B2 | 11/2010 | Kizer et al. |
| 7,838,040 | B2 | 11/2010 | Malinin |
| 7,875,296 | B2 | 1/2011 | Binette et al. |
| 7,879,604 | B2 | 2/2011 | Seyedin et al. |
| RE42,208 | E | 3/2011 | Truncale et al. |
| 7,897,384 | B2 | 3/2011 | Binette et al. |
| 7,901,457 | B2 | 3/2011 | Truncale et al. |
| 7,901,461 | B2 | 3/2011 | Harmon et al. |
| 8,017,394 | B2 | 9/2011 | Adkisson, IV et al. |
| 8,025,901 | B2 | 9/2011 | Kao et al. |
| 8,137,702 | B2 | 3/2012 | Binette et al. |
| 8,163,549 | B2 | 4/2012 | Yao et al. |
| 2001/0006634 | A1 | 7/2001 | Zaleske et al. |
| 2001/0014473 | A1 | 8/2001 | Rieser |
| 2001/0014475 | A1 | 8/2001 | Frondoza et al. |

| | | |
|---|---|---|
| 2001/0051834 A1 | 12/2001 | Frondoza et al. |
| 2001/0055621 A1 | 12/2001 | Baugh et al. |
| 2002/0004038 A1 | 1/2002 | Baugh et al. |
| 2002/0009805 A1 | 1/2002 | Nevo et al. |
| 2002/0012705 A1 | 1/2002 | Domb |
| 2002/0028192 A1 | 3/2002 | Dimitrijevich et al. |
| 2002/0029055 A1 | 3/2002 | Bonutti |
| 2002/0055755 A1 | 5/2002 | Bonutti |
| 2002/0062151 A1 | 5/2002 | Altman et al. |
| 2002/0064512 A1 | 5/2002 | Petersen et al. |
| 2002/0082623 A1 | 6/2002 | Osther et al. |
| 2002/0095160 A1 | 7/2002 | Bonutti |
| 2002/0099401 A1 | 7/2002 | Bonutti |
| 2002/0099448 A1 | 7/2002 | Hiles et al. |
| 2002/0106625 A1 | 8/2002 | Hung et al. |
| 2002/0123142 A1 | 9/2002 | Hungerford et al. |
| 2002/0128683 A1 | 9/2002 | Epstein |
| 2002/0133235 A1 | 9/2002 | Hungerford et al. |
| 2002/0150550 A1 | 10/2002 | Petersen |
| 2002/0151974 A1 | 10/2002 | Bonassar et al. |
| 2002/0159982 A1 | 10/2002 | Bonassar et al. |
| 2002/0159985 A1 | 10/2002 | Baugh et al. |
| 2002/0183850 A1 | 12/2002 | Felt et al. |
| 2002/0198490 A1 | 12/2002 | Wirt et al. |
| 2002/0198599 A1 | 12/2002 | Haldimann |
| 2003/0009147 A1 | 1/2003 | Bonutti |
| 2003/0009235 A1 | 1/2003 | Manrique et al. |
| 2003/0039695 A1 | 2/2003 | Geistlich et al. |
| 2003/0040113 A1 | 2/2003 | Mizuno et al. |
| 2003/0065389 A1 | 4/2003 | Petersen |
| 2003/0069605 A1 | 4/2003 | Bonutti et al. |
| 2003/0077244 A1 | 4/2003 | Petersen |
| 2003/0099620 A1 | 5/2003 | Zaleske et al. |
| 2003/0114936 A1 | 6/2003 | Sherwood et al. |
| 2003/0134032 A1 | 7/2003 | Chaouk et al. |
| 2003/0151974 A1 | 8/2003 | Kutty et al. |
| 2003/0153078 A1 | 8/2003 | Libera et al. |
| 2003/0176602 A1 | 9/2003 | Schmidt et al. |
| 2003/0181939 A1 | 9/2003 | Bonutti |
| 2003/0187387 A1 | 10/2003 | Wirt et al. |
| 2003/0195628 A1 | 10/2003 | Bao et al. |
| 2003/0211073 A1 | 11/2003 | Goupil et al. |
| 2003/0223956 A1 | 12/2003 | Goupil et al. |
| 2004/0030404 A1 | 2/2004 | Noll et al. |
| 2004/0030406 A1 | 2/2004 | Ochi |
| 2004/0033212 A1 | 2/2004 | Thomson et al. |
| 2004/0042960 A1 | 3/2004 | Frey et al. |
| 2004/0044408 A1 | 3/2004 | Hungerford et al. |
| 2004/0048796 A1 | 3/2004 | Hariri et al. |
| 2004/0059416 A1 | 3/2004 | Murray et al. |
| 2004/0064192 A1 | 4/2004 | Bubb |
| 2004/0064193 A1 | 4/2004 | Evans et al. |
| 2004/0073308 A1 | 4/2004 | Kuslich et al. |
| 2004/0078073 A1 | 4/2004 | Bonutti |
| 2004/0078077 A1 | 4/2004 | Binette et al. |
| 2004/0078090 A1 | 4/2004 | Binette et al. |
| 2004/0092946 A1 | 5/2004 | Bagga et al. |
| 2004/0097714 A1 | 5/2004 | Maubois et al. |
| 2004/0097829 A1 | 5/2004 | McRury et al. |
| 2004/0117033 A1 | 6/2004 | Frondoza |
| 2004/0127987 A1 | 7/2004 | Evans et al. |
| 2004/0134502 A1 | 7/2004 | Mizuno et al. |
| 2004/0138522 A1 | 7/2004 | Haarstad et al. |
| 2004/0151705 A1 | 8/2004 | Mizuno et al. |
| 2004/0172045 A1 | 9/2004 | Eriksson et al. |
| 2004/0175690 A1 | 9/2004 | Mishra et al. |
| 2004/0176787 A1 | 9/2004 | Mishra et al. |
| 2004/0181240 A1 | 9/2004 | Tseng et al. |
| 2004/0191900 A1 | 9/2004 | Mizuno et al. |
| 2004/0193181 A1 | 9/2004 | Bonutti |
| 2004/0219182 A1 | 11/2004 | Gomes et al. |
| 2004/0228901 A1 | 11/2004 | Trieu et al. |
| 2004/0230303 A1 | 11/2004 | Gomes et al. |
| 2004/0230309 A1 | 11/2004 | DiMauro et al. |
| 2005/0026133 A1 | 2/2005 | Nakatsuji et al. |
| 2005/0038520 A1 | 2/2005 | Bienette et al. |
| 2005/0043805 A1 | 2/2005 | Chudik |
| 2005/0043814 A1 | 2/2005 | Kusanagi et al. |
| 2005/0054595 A1 | 3/2005 | Bienette et al. |
| 2005/0064042 A1 | 3/2005 | Vunjak-novakovic et al. |
| 2005/0079159 A1 | 4/2005 | Shastri et al. |
| 2005/0095235 A1 | 5/2005 | Austin et al. |
| 2005/0095666 A1 | 5/2005 | Jhavar et al. |
| 2005/0113736 A1 | 5/2005 | Orr et al. |
| 2005/0113937 A1 | 5/2005 | Binette et al. |
| 2005/0119754 A1 | 6/2005 | Trieu et al. |
| 2005/0123520 A1 | 6/2005 | Eavey et al. |
| 2005/0124038 A1 | 6/2005 | Aguiar et al. |
| 2005/0125077 A1 | 6/2005 | Harmon et al. |
| 2005/0136046 A1 | 6/2005 | Pines et al. |
| 2005/0137600 A1 | 6/2005 | Jacobs et al. |
| 2005/0139656 A1 | 6/2005 | Arnouse |
| 2005/0152882 A1 | 7/2005 | Kizer et al. |
| 2005/0152886 A1 | 7/2005 | Baugh |
| 2005/0152961 A1 | 7/2005 | Austin et al. |
| 2005/0171470 A1 | 8/2005 | Kucklick et al. |
| 2005/0175657 A1 | 8/2005 | Hunter et al. |
| 2005/0175704 A1 | 8/2005 | Petersen |
| 2005/0175711 A1 | 8/2005 | Kralovec et al. |
| 2005/0177249 A1 | 8/2005 | Kladakis et al. |
| 2005/0186247 A1 | 8/2005 | Hunter |
| 2005/0186283 A1 | 8/2005 | Geistlich et al. |
| 2005/0186673 A1 | 8/2005 | Geistlich et al. |
| 2005/0192532 A1 | 9/2005 | Kucklick et al. |
| 2005/0196387 A1 | 9/2005 | Seyedin et al. |
| 2005/0196460 A1 | 9/2005 | Malinin |
| 2005/0203342 A1 | 9/2005 | Kucklick et al. |
| 2005/0209601 A1 | 9/2005 | Bowman et al. |
| 2005/0209602 A1 | 9/2005 | Bowman et al. |
| 2005/0222687 A1 | 10/2005 | Vunjak-Novakovic et al. |
| 2005/0226856 A1 | 10/2005 | Ahlfors |
| 2005/0234298 A1 | 10/2005 | Kucklick et al. |
| 2005/0234485 A1 | 10/2005 | Seegert et al. |
| 2005/0244454 A1 | 11/2005 | Elson et al. |
| 2005/0250697 A1 | 11/2005 | Maubois et al. |
| 2005/0250698 A1 | 11/2005 | Maubois et al. |
| 2005/0251268 A1 | 11/2005 | Truncale |
| 2005/0265980 A1 | 12/2005 | Chen et al. |
| 2005/0267584 A1 | 12/2005 | Burdulis, Jr. et al. |
| 2005/0273129 A1 | 12/2005 | Michels et al. |
| 2005/0287218 A1 | 12/2005 | Chaouk et al. |
| 2005/0288796 A1 | 12/2005 | Awad et al. |
| 2006/0008530 A1 | 1/2006 | Seyedin et al. |
| 2006/0009779 A1 | 1/2006 | Collins et al. |
| 2006/0019389 A1 | 1/2006 | Yayon et al. |
| 2006/0024373 A1 | 2/2006 | Shahar et al. |
| 2006/0024826 A1 | 2/2006 | Bonassar et al. |
| 2006/0029679 A1 | 2/2006 | Dolecek |
| 2006/0041270 A1 | 2/2006 | Lenker et al. |
| 2006/0073588 A1 | 4/2006 | Adkisson et al. |
| 2006/0078872 A1 | 4/2006 | Taguchi et al. |
| 2006/0099706 A1 | 5/2006 | Massey et al. |
| 2006/0111738 A1 | 5/2006 | Wenchell |
| 2006/0111778 A1 | 5/2006 | Michalow |
| 2006/0128016 A1 | 6/2006 | Tokushima et al. |
| 2006/0134093 A1 | 6/2006 | Ronfard |
| 2006/0134094 A2 | 6/2006 | Delmotte et al. |
| 2006/0147547 A1 | 7/2006 | Yayon |
| 2006/0153815 A1 | 7/2006 | Seyda et al. |
| 2006/0183224 A1 | 8/2006 | Aerts et al. |
| 2006/0195188 A1 | 8/2006 | O'Driscoll et al. |
| 2006/0210643 A1 | 9/2006 | Truncale et al. |
| 2006/0216822 A1 | 9/2006 | Mizuno et al. |
| 2006/0228391 A1 | 10/2006 | Seyedin et al. |
| 2006/0240064 A9 | 10/2006 | Hunter et al. |
| 2006/0240555 A1 | 10/2006 | Ronfard |
| 2006/0251631 A1 | 11/2006 | Adkisson et al. |
| 2006/0264966 A1 | 11/2006 | Armstrong |
| 2006/0275273 A1 | 12/2006 | Seyedin et al. |
| 2006/0281173 A1 | 12/2006 | Fukuda et al. |
| 2006/0292131 A1 | 12/2006 | Binette et al. |
| 2007/0014867 A1 | 1/2007 | Kusanagi |
| 2007/0031471 A1 | 2/2007 | Peyman |
| 2007/0038299 A1 | 2/2007 | Stone |
| 2007/0041952 A1 | 2/2007 | Guilak et al. |
| 2007/0077236 A1 | 4/2007 | Osther |
| 2007/0087032 A1 | 4/2007 | Chang et al. |
| 2007/0098759 A1 | 5/2007 | Malinin |

| | | | | | | |
|---|---|---|---|---|---|---|
| 2007/0106394 A1 | 5/2007 | Chen | CA | 2563082 A1 | 11/2005 |
| 2007/0128155 A1 | 6/2007 | Seyedin et al. | CA | 2570521 A1 | 3/2006 |
| 2007/0191781 A1 | 8/2007 | Richards et al. | CA | 2631520 A1 | 6/2007 |
| 2007/0212389 A1 | 9/2007 | Weiss et al. | CA | 2708147 A1 | 6/2009 |
| 2007/0213660 A1 | 9/2007 | Richards et al. | CA | 2717725 A1 | 9/2009 |
| 2007/0250164 A1 | 10/2007 | Troxel | EP | 0006216 A1 | 1/1980 |
| 2007/0292945 A1 | 12/2007 | Lin et al. | EP | 0133934 A2 | 3/1985 |
| 2007/0299517 A1 | 12/2007 | Davisson | EP | 0341007 A2 | 11/1989 |
| 2008/0009942 A1 | 1/2008 | Mizuno et al. | EP | 0493387 B1 | 10/1993 |
| 2008/0031934 A1 | 2/2008 | MacPhee et al. | EP | 0592242 A1 | 4/1994 |
| 2008/0033331 A1 | 2/2008 | MacPhee et al. | EP | 0641007 A2 | 3/1995 |
| 2008/0033332 A1 | 2/2008 | MacPhee et al. | EP | 0654078 B1 | 5/1995 |
| 2008/0033333 A1 | 2/2008 | MacPhee et al. | EP | 0669138 A2 | 8/1995 |
| 2008/0039940 A1 | 2/2008 | Hashimoto et al. | EP | 0610423 B1 | 5/1997 |
| 2008/0039954 A1 | 2/2008 | Long | EP | 0877632 B1 | 9/1997 |
| 2008/0051624 A1 | 2/2008 | Bonutti | EP | 0867193 A2 | 9/1998 |
| 2008/0065210 A1 | 3/2008 | McKay | EP | 0920490 A2 | 6/1999 |
| 2008/0071385 A1 | 3/2008 | Binette et al. | EP | 01010356 A1 | 6/2000 |
| 2008/0081369 A1 | 4/2008 | Adkisson, IV et al. | EP | 1142581 A2 | 10/2001 |
| 2008/0103564 A1 | 5/2008 | Burkinshaw et al. | EP | 1003568 B1 | 4/2003 |
| 2008/0113007 A1 | 5/2008 | Kurihara et al. | EP | 0592242 B1 | 7/2003 |
| 2008/0153157 A1 | 6/2008 | Yao et al. | EP | 0906069 B1 | 2/2004 |
| 2008/0154370 A1 | 6/2008 | Mathies | EP | 1410810 A1 | 4/2004 |
| 2008/0199429 A1 | 8/2008 | Hollander et al. | EP | 1410811 A1 | 4/2004 |
| 2008/0274157 A1 | 11/2008 | Vunjak-Novakovic et al. | EP | 1433423 A1 | 6/2004 |
| 2008/0299214 A1 | 12/2008 | Seyedin et al. | EP | 1471140 A1 | 10/2004 |
| 2009/0012629 A1 | 1/2009 | Yao et al. | EP | 1506790 A1 | 2/2005 |
| 2009/0069901 A1 | 3/2009 | Truncale et al. | EP | 1512739 A1 | 3/2005 |
| 2009/0143867 A1 | 6/2009 | Gage et al. | EP | 1535578 A1 | 6/2005 |
| 2009/0149893 A1 | 6/2009 | Semler et al. | EP | 1535633 A1 | 6/2005 |
| 2009/0155229 A1 | 6/2009 | Yayon | EP | 1537883 A2 | 6/2005 |
| 2009/0181092 A1 | 7/2009 | Thorne et al. | EP | 1538196 A1 | 6/2005 |
| 2009/0181093 A1 | 7/2009 | Thorne et al. | EP | 1537883 A3 | 8/2005 |
| 2009/0181892 A1 | 7/2009 | Thorne et al. | EP | 1561481 A2 | 8/2005 |
| 2009/0214614 A1 | 8/2009 | Everland et al. | EP | 1599126 A2 | 11/2005 |
| 2009/0291112 A1 | 11/2009 | Truncale | EP | 1387703 B1 | 7/2006 |
| 2009/0319045 A1 | 12/2009 | Truncale et al. | EP | 1303184 B1 | 9/2006 |
| 2010/0015202 A1 | 1/2010 | Semler et al. | EP | 1410810 B1 | 1/2007 |
| 2010/0086594 A1 | 4/2010 | Amit et al. | EP | 1561481 A3 | 3/2008 |
| 2010/0121311 A1 | 5/2010 | Seegert et al. | EP | 1537883 B1 | 4/2008 |
| 2010/0168856 A1 | 7/2010 | Long et al. | EP | 1618178 B1 | 7/2008 |
| 2010/0209397 A1 | 8/2010 | Maor | EP | 1410811 B1 | 10/2008 |
| 2010/0209408 A1 | 8/2010 | Stephen A. et al. | EP | 1433423 B1 | 12/2008 |
| 2010/0274362 A1 | 10/2010 | Yayon et al. | EP | 2335650 A1 | 6/2011 |
| 2010/0303765 A1 | 12/2010 | Athanasiou et al. | EP | 2338441 A1 | 6/2011 |
| 2010/0322994 A1 | 12/2010 | Kizer et al. | EP | 2338442 A1 | 6/2011 |
| 2011/0009963 A1 | 1/2011 | Binnette et al. | EP | 2338533 A1 | 6/2011 |
| 2011/0052705 A1 | 3/2011 | Malinin | EP | 1691727 B1 | 7/2011 |
| 2011/0070271 A1 | 3/2011 | Truncale et al. | EP | 2101681 | 8/2011 |
| 2011/0091517 A1 | 4/2011 | Binette et al. | EP | 1958651 B1 | 10/2011 |
| 2011/0097381 A1 | 4/2011 | Binette et al. | EP | 1561481 B1 | 3/2012 |
| 2011/0166669 A1 | 7/2011 | Truncale et al. | EP | 1753860 B1 | 4/2012 |
| 2011/0177134 A1 | 7/2011 | Harmon et al. | EP | 2335650 B1 | 10/2012 |
| 2011/0196508 A1 | 8/2011 | Truncale et al. | EP | 2338441 B1 | 1/2013 |
| 2011/0256095 A1 | 10/2011 | Seyedin et al. | GB | 2105198 A | 3/1983 |
| 2012/0009224 A1 | 1/2012 | Kizer et al. | GB | 2175507 A | 12/1986 |
| 2012/0009270 A1 | 1/2012 | Kizer et al. | GB | 2404607 A | 9/2005 |
| 2012/0107384 A1 | 5/2012 | Yao et al. | JP | 59135054 A | 8/1984 |
| 2012/0156265 A1 | 6/2012 | Binette et al. | JP | 10036534 A | 2/1998 |
| 2012/0239146 A1 | 9/2012 | Kizer et al. | JP | 2002233567 A | 8/2002 |
| | | | JP | 2004136096 A | 5/2004 |
| FOREIGN PATENT DOCUMENTS | | | JP | 2006230749 A | 9/2006 |
| | | | JP | 2003102755 A | 4/2008 |
| CA | 2261292 C | 2/1998 | WO | WO-8002501 A1 | 11/1980 |
| CA | 2261292 A1 | 1/1999 | WO | WO-8505274 A1 | 12/1985 |
| CA | 2441994 A1 | 10/2002 | WO | WO-9000060 A1 | 1/1990 |
| CA | 2445356 A1 | 4/2004 | WO | WO-9101711 A1 | 2/1991 |
| CA | 2445356 C | 4/2004 | WO | WO-9209697 A1 | 6/1992 |
| CA | 2445558 A1 | 4/2004 | WO | WO-9603112 A1 | 2/1996 |
| CA | 2445558 C | 4/2004 | WO | WO-9603160 A1 | 2/1996 |
| CA | 2449227 A1 | 5/2004 | WO | WO-9639170 A1 | 12/1996 |
| CA | 2449227 C | 5/2004 | WO | WO-9711090 A1 | 3/1997 |
| CA | 2522133 A1 | 11/2004 | WO | WO-9726847 A1 | 7/1997 |
| CA | 2522133 C | 11/2004 | WO | WO-9804681 A2 | 2/1998 |
| CA | 2475905 A1 | 2/2005 | WO | WO-9844874 A1 | 10/1998 |
| CA | 2475905 C | 2/2005 | WO | WO-9907417 A1 | 2/1999 |
| CA | 2480712 A1 | 3/2005 | WO | WO-9951164 A1 | 10/1999 |
| CA | 2487029 A1 | 5/2005 | WO | WO-0006216 A1 | 2/2000 |
| CA | 2487042 A1 | 6/2005 | WO | WO-0029484 A1 | 5/2000 |
| CA | 2496184 A1 | 8/2005 | | | |

| | | | |
|---|---|---|---|
| WO | WO-0048837 A1 | 8/2000 |
| WO | WO-0056251 A1 | 9/2000 |
| WO | WO-0062832 A1 | 10/2000 |
| WO | WO-0074741 A2 | 12/2000 |
| WO | WO-0074741 A3 | 12/2000 |
| WO | WO-0102030 A2 | 1/2001 |
| WO | WO-0105443 A1 | 1/2001 |
| WO | WO-0110356 A2 | 2/2001 |
| WO | WO-0123014 A1 | 4/2001 |
| WO | WO-0167961 A1 | 9/2001 |
| WO | WO-0168811 A2 | 9/2001 |
| WO | WO-0168811 A3 | 9/2001 |
| WO | WO-0185225 A2 | 11/2001 |
| WO | WO-0197872 A1 | 12/2001 |
| WO | WO-0185225 A3 | 3/2002 |
| WO | WO-0224244 A2 | 3/2002 |
| WO | WO-02067856 A2 | 9/2002 |
| WO | WO-02076285 A2 | 10/2002 |
| WO | WO-02080991 A2 | 10/2002 |
| WO | WO-02089868 A1 | 11/2002 |
| WO | WO-03077794 A2 | 9/2003 |
| WO | WO-03093433 A2 | 11/2003 |
| WO | WO-03100417 A1 | 12/2003 |
| WO | WO-2004028547 A1 | 4/2004 |
| WO | WO-2004028584 A1 | 4/2004 |
| WO | WO-03093433 A3 | 7/2004 |
| WO | WO-2004078032 A2 | 9/2004 |
| WO | WO-2004078032 A3 | 9/2004 |
| WO | WO-2004078035 A2 | 9/2004 |
| WO | WO-2004078955 A1 | 9/2004 |
| WO | WO-2004096983 A2 | 11/2004 |
| WO | WO-2004105576 A2 | 12/2004 |
| WO | WO-2004110308 A2 | 12/2004 |
| WO | WO-2004110512 A2 | 12/2004 |
| WO | WO-2005011765 A1 | 2/2005 |
| WO | WO-2005018491 A2 | 3/2005 |
| WO | WO-2004110512 A3 | 5/2005 |
| WO | WO-2005044326 A1 | 5/2005 |
| WO | WO-2005058207 A1 | 6/2005 |
| WO | WO-2005060987 A1 | 7/2005 |
| WO | WO-2005061018 A1 | 7/2005 |
| WO | WO-2005061019 A2 | 7/2005 |
| WO | WO-2005065079 A2 | 7/2005 |
| WO | WO-2005081870 A2 | 9/2005 |
| WO | WO-2005092208 A1 | 10/2005 |
| WO | WO-2005092405 A1 | 10/2005 |
| WO | WO-2005110278 A2 | 11/2005 |
| WO | WO-2005113751 A1 | 12/2005 |
| WO | WO-2006002253 A2 | 1/2006 |
| WO | WO-2006002253 A3 | 1/2006 |
| WO | WO-2006017176 A2 | 2/2006 |
| WO | WO-2006033698 A2 | 3/2006 |
| WO | WO-2006039484 A2 | 4/2006 |
| WO | WO-2006068972 A2 | 6/2006 |
| WO | WO-2006033698 A3 | 7/2006 |
| WO | WO-2006090372 A2 | 8/2006 |
| WO | WO-2006090372 A3 | 8/2006 |
| WO | WO-2006113642 A1 | 11/2006 |
| WO | WO-2006121612 A1 | 11/2006 |
| WO | WO-2005081870 A3 | 12/2006 |
| WO | WO-2006039484 A3 | 1/2007 |
| WO | WO-2007025290 A2 | 3/2007 |
| WO | WO-2007054939 A2 | 5/2007 |
| WO | WO-2007067637 A2 | 6/2007 |
| WO | WO-2007089942 A2 | 8/2007 |
| WO | WO-2007089948 A2 | 8/2007 |
| WO | WO-2007102149 A2 | 9/2007 |
| WO | WO-2007025290 A3 | 10/2007 |
| WO | WO-2007115336 A2 | 10/2007 |
| WO | WO-2007143726 A2 | 12/2007 |
| WO | WO-2007089948 A3 | 1/2008 |
| WO | WO-2008019127 A2 | 2/2008 |
| WO | WO-2008019128 A2 | 2/2008 |
| WO | WO-2008019129 A2 | 2/2008 |
| WO | WO-2008021127 A2 | 2/2008 |
| WO | WO-2008079194 A1 | 7/2008 |
| WO | WO-2008079613 A1 | 7/2008 |
| WO | WO-2008106254 A2 | 9/2008 |
| WO | WO-2008128075 A1 | 10/2008 |
| WO | WO-2009039469 A1 | 3/2009 |
| WO | WO-2009076164 A2 | 6/2009 |
| WO | WO-2009111069 A1 | 9/2009 |
| WO | WO-2010078040 A1 | 7/2010 |

OTHER PUBLICATIONS

U.S. Appl. No. 11/613,250, Advisory Action mailed Jul. 9, 2008, 13 pgs.
U.S. Appl. No. 11/613,250, Final Office Action mailed Apr. 15, 2008, 9 pgs.
U.S. Appl. No. 11/613,250, Non Final Office Action mailed Mar. 28, 2011, 9 pgs.
U.S. Appl. No. 11/613,250, Non Final Office Action mailed May 28, 2009, 12 pgs.
U.S. Appl. No. 11/613,250, Non Final Office Action mailed Sep. 20, 2007, 17 pgs.
U.S. Appl. No. 11/613,250, Non Final Office Action mailed Sep. 21, 2010, 15 pgs.
U.S. Appl. No. 11/613,250, Non Final Office Action mailed Oct. 16, 2008, 11 pgs.
U.S. Appl. No. 11/613,250, Non Final Office Action mailed Dec. 23, 2009, 15 pgs.
U.S. Appl. No. 11/613,250, Notice of Allowance mailed Dec. 23, 2011, 9 pgs.
U.S. Appl. No. 11/613,250, Response filed Jan. 16, 2009 to Non Final Office Action mailed Oct. 16, 2008, 9 pgs.
U.S. Appl. No. 11/613,250, Response filed Jan. 19, 2011 to Non Final Office Action mailed Sep. 21, 2010, 13 pgs.
U.S. Appl. No. 11/613,250, Response filed Mar. 23, 2010 to Non Final Office Action mailed Dec. 23, 2009, 9 pgs.
U.S. Appl. No. 11/613,250, Response filed Jun. 16, 2008 to Final Office Action mailed Apr. 15, 2008, 19 pgs.
U.S. Appl. No. 11/613,250, Response filed Aug. 28, 2009 to Non Final Office Action mailed May 28, 2009, 12 pgs.
U.S. Appl. No. 11/613,250, Response filed Sep. 28, 2011 to Non Final Office Action mailed Mar. 28, 2011, 9 pgs.
U.S. Appl. No. 11/613,250, Response filed Dec. 20, 2007 to Non Final Office Action mailed Sep. 20, 2007, 19 pgs.
International Application U.S. Appl. No. PCT/US2007/025252, International Search Report mailed Apr. 18, 2008, 3 pgs.
Albrecht, F., et al., "Closure of Osteochondral Lesions Using Chondral Fragments and Fibrin Adhesive", Arch. Orthop. Trauma surg. 101, (1983), 213-217.
Aston, Jayne E, et al., "Repair of Articular Surfaces by Allografts of Articular and Growth-Plate Cartilage", vol. 68-B, No. I, British Editorial Society of Bone and Joint Surgery, England, (1986), 29-35.
Bacsich, P., et al., "The Significance of the Mucoprotein Content on the Survival of Homografts of Cartilage and Cornea", Department of Anatomy University of Glasgow, vol. LXII, (1946), 322-329.
Bayliss, Michael, et al., "The properties of proteoglycan prepared from human articular cartilage by using 1 associative caesium chloride gradients of high and low starting densities", Biochem. J., vol. 232, Great Britain, (1985), 111-117.
Bentley, George, et al., "Homotransplantation of isolated epiphyseal and articular cartilage chondrocytes into joint surfaces of rabbits", Nature 230, (1971), 385 388.
Berlet, G.C., et al., "Treatment of Unstable Osteochondritis Dissecans Lesions of the Knee Using Autogenous Osteochondral Grafts (Mosaicplasty)", Arthroscopy 15-3, (1999), 312-316.
Brittberg, M., et al., "Treatment of Deep Cartilage Defects in the Knee with Autologous Chondrocyte Transplantation", N. Engl. J. Med. 331-14, (1994), 889-895.
Brittberg, Mats, "Autologous Chondrocyte Transplantation, Clinical Orthopaedics and Related Research,", vol. 367S, Lippincott Williams & Wilkins, Inc., (1999), 147-155.
Bruns, J., et al., "Autologous rib perichondrial grafts in experimentally induced osteochondral lesions in the sheep-knee joint: morphological results", Virchows Archiv A Pathol Anat 421, (1992), 1-8.
Buckwalter, J. A., "Articular Cartilage Injuries", Clinical Orthopaedics and Related Research, No. 402, (2002), 21-37.

Chen, Frank S, et al., "Repair of articular cartilage defects: Part II treatment options", The American Journal of Orthopedics 28(2), (1999), 88-96.

Convery, F.R., et al., "The Repair of Large Osteochondral Defects", An Experimental Study in Horses, Clin. Orthrop. 82., (1972), 253-262.

Coster, D., et al., "Diced cartilage grafts to correct enophthalmos", British Journal of Ophthamology, vol. 64, (1980), 135-136.

Craigmyle, M. B., "Studies of cartilage autografts and homografts in the rabbit", British Journal of Plastic Surgery 8, (1955), 93-100.

De Kleine, "A Simplified Method for Handling of Diced Cartilage", Plast Reconstr. Surg., vol. 3, (1948), 95-102.

Dupertuis, S., "Actual Growth of Young Cartilage Transplants in Rabbits", Archives of Surgery, vol. 43, (1941), 32-63.

Erol, et al., "The Turkish Delight: A Pliable Graft for Rhinoplasty,", Plas!. Reconstr. Surg., vol. 105, (2000), 2229-2241.

Fontana, A., et al., "Cartilage Chips Synthesized with Fibrin Glue in Rhinoplasty", Aesthy. Plast. Surg.15, (1991), 237-240.

Ghazavi, M. T, et al., "Fresh Osteochondral Allografts for Post-Traumatic Osteochondral Defects of the Knee", J. Bone Joint Surg., 79-B, (1997), 1008-1013.

Gibson, Thomas, et al., "The long-term survival of cartilage homografts in man", British Journal of Plastic Surgery 11, (1958), 177-187.

Hangody, Laszlo, et al., "Autogenous Osteochondral Graft Technique for Replacing Knee Cartilage Defects in Dogs", Autogenous Osteochondral Mosaicplasty—Orthopaedics International Ed., vol. 5, No. 3, (1997), 175-181.

Homminga, G., et al., "Perichondral grafting for cartilage lesions of the knee", J. Bone Joint Surg. (Br.) 72-B, (1990), 1003-1007.

Horas, U., et al., "Autologous Chondrocyte Implantation and Osteochondral Cylinder Transplantation in Cartilage Repair of the Knee Joint: A Prospective", Comparative Trial, J. Bone Joint Surg. Am. 85A-2, (2003), 185-192.

Hunziker, E. B., "Articular cartilage repair: basic science and clinical progress—a review of the current status and prospects", Osteoarthritis and Cartilage 10(6), (2001), 432-463.

Hurtig, M. B, "Use of autogenous cartilage particles to create a model of naturally occurring degenerative joint disease in the horse", Equine Orthop., No. 6, (1988), 19-22.

Johnson, L., "Arthroscopic Abrasion Arthroplasty Historical and Pathologic Perspective: Present Status", Arthroscopy 2-1, (1986), 54-69.

Kaplonyi, G., et al., "The use of fibrin adhesive in the repair of chondral and osteochondral injuries", Injury 19, (1988), 267-272.

Knutsen, G., et al., "Autologous Chondrocyte Implantation Compared with Microfracture in the Knee. A Randomized Trial", J. Bone Joint Surg. Am. 86A-3, (2004), 455-464.

Leopold, G., "Experimental Studies into the Etiology of Tumors", Archiv. F. Path. Anat., vol. LXXXV, No. 2, (1881), 283-324.

Lu, Yiling, et al., "Minced Cartilage Without Cell Culture Serves as an Effective Intraoperative Cell Source for Cartilage Repair", Journal of Orthopaedic Research, 24(6), (Jun. 2006), 1261-1270.

Mahomed, M.N., et al., "The Long-Term Success of Fresh, Small Fragment Osteochondral Alografts Used for Intraarticular Post-Traumatic Defects in the Knee Joint", Orthopedics 15, (1992), 1191-1199.

Mainil-Varlet, P, et al., "Articular cartilage repair using a tissue-engineered cartilage-like implant: an animal study", Osteoarthritis Cartilage Suppl. A, vol. 9, (2001), 6-15.

Marcacci, et al., "Articular Cartilage Engineering with Hyalograft C", Clinical Orthopaedics & Related Research, V. 435, (Jun. 2005), 96-105.

Meachim, G., et al., "Repair of the joint surface from subarticular tissue in the rabbit knee", J. Anat. 109-2, (1971), 317-327.

Mitchell, Nelson, et al., "The Resurfacing of Adult Rabbit Articular Cartilage by Multiple Perforations through the Subchondral Bone", J. Bone Joint Surg. 58A-2, (1976), 230-233.

Nixon, Alan, et al., "Isolation, propagation, and cryopreservation of equine articular chondrocytes", American Journal of Veterinary Research, 53(12), (1992), 2364-2370.

Nixon, Alan J, et al., "New Horizons in Articular Cartilage", Proceedings of the 47th Annual American Association of Equine Practitioners Convention, V. 47, (2001), 217-226.

O'Driscoll, Shawn W, et al., "The Repair of Major Osteochondral Defects in Joint Surfaces by Neochondrogenesis with Autogenous Osteoperiosteal Grafts Stimulated by Continuous Passive Motion", Clinical Orthopaedics and Related Research, No. 208 Canada, (1986), 131-140.

Paccola, Cleber, et al., "Fresh Immature Articular Cartilage Allografts—A Study on the Integration of Chondral 11 and Osteochondral Grafts Both in Normal and in Papain-Treated Knee Joints of Rabbits", Arch. Orthop. Trauma!. Surg., vol. 93, (1979), 253-259.

Passl, R., et al., "Using Fibrin to Glue and Flatten Cartilage", Beitr. Orthrop. Tramatol 36, (1989), 503-507.

Peer, Lyndon, "Diced Cartilage Grafts—New Method for Repair of Skull Defects, Mastoid Fistula and Other Deformities", Archives of Otolaryngology, vol. 38, No. 2, (1943), 156-165.

Peretti, Giuseppe M, et al., "Biomechanical analysis of a chondrocyte-based repair model of articular cartilage", Tissue Engineering 5(4), (1999), 317-326.

Peretti, Giuseppe M, et al., "Bonding of cartilage matrices with cultured chondrocytes: an experimental model", Journal of Orthopaedic Research 16(1), (1998), 89-95.

Peretti, Giuseppe M, et al., "Cell-based bonding of articular cartilage: An extended study", Wiley Periodicals, Inc., (2003), 517-524.

Peretti, Giuseppe M, et al., "In vitro bonding of pre-seeded chondrocytes", Sport Sciences for Health, V. 2, (2007), 29-33.

Plenk, Jr, et al., "Articular Cartilage Transplants in Experiments and Clinical Practice", ACA, Acta Chirurgica Austriaca, vol. 29, No. 137, (1997), 2-4.

Pridie, K.A., et al., "A method of resurfacing osteoarthritic knee joints", J. Bone Joint Surg. 41B-3, (1959), 618-619.

Prudden MD, T. Mitchell, "Experimental Studies on the Transplantation of Cartilage", The American Journal of the Medical Sciences vol. LXXXI, (1881), 360-370.

Robinson, Dror, et al., "Regenerating Hyaline Cartilage in Articular Defects of Old Chickens Using Implants of Embryonal Chick Chondrocytes Embedded in a New Natural Delivery Substance", Calcified Tissue International, vol. 46, Springer-Verlag New York Inc., USA, (1990), 246-253.

Silverman, Ronald P, et al., "Injectable Tissue-Engineered Cartilage Using a Fibrin Glue Polymer", Plastic & Reconstructive Surgery vol. 103 (7), (1999), 1809-1818.

Specchia, Nicola, et al., "Fetal Chondral Homographs in the Repair of Articular Cartilage Defects", Bulletin of the Hospital for Joint Diseases vol. 54 (4), (1996), 230-235.

Stoksted, et al., "Crushed cartilage in nasal reconstruction", J. Laryng. Otol., vol. 100, (1986), 897-906.

Temenoff, J.S., et al., "Review: tissue engineering for regeneration of articular cartilage", Biomaterials 21, (2000), 431-440.

Wakitani, Shigeyuki, et al., "Repair of Rabbit Articular Surfaces with Allograft Chondrocytes Embedded in Collagen Gel", J. Bone Joint Surg., vol. 71-B, (1989), 74-80.

Xu, Jian-Wei, et al., "Injectable tissue-engineered cartilage with different chondrocyte sources", Plast Reconstr Surg., 113(5), (Apr. 15, 2004), 1361-71.

Yamamoto, Etsuo, et al., "Use of Micro-Sliced Homograft Cartilage Plates in Tympanoplasty", Acta Otolaryngol., suppl. 419, (1985), 123-129.

Yamashita, F., et al., "The Transplantatoin of Autogeneic Osteochondral Fragment for Osteochondritis Dissecans of the Knee", Orthopedics 15, (1992), 1191-1199.

Yilmaz, Sarper, et al., "Viability of Diced, Crushed Cartilage Grafts and the Effects of Surgical (Oxidized Regenerated Cellulose) on Cartilage Grafts", Plastic & Reconstructive Surgery 108(4), (2001), 1054-1060.

Zah, F., "WilhSort Des Tissus Implantes Dan L'Organisme", Cong Med Int DeGeneve, (Sep. 11, 1877).

U.S. Appl. No. 11/010,779, Examiner Interview Summary mailed Apr. 5, 2010, 4 pgs.

U.S. Appl. No. 11/010,779, Examiner Interview Summary mailed Dec. 7, 2009, 3 pgs.

U.S. Appl. No. 11/010,779, Non Final Office Action mailed Feb. 17, 2010, 4 pgs.
U.S. Appl. No. 11/010,779, Non Final Office Action mailed Apr. 15, 2009, 8 pgs.
U.S. Appl. No. 11/010,779, Notice of Allowance mailed Jul. 8, 2010, 4 pgs.
U.S. Appl. No. 11/010,779, Response filed Feb. 12, 2009 to Restriction Requirement mailed Jan. 12, 2009, 3 pgs.
U.S. Appl. No. 11/010,779, Response filed Apr. 19, 2010 to Non Final Office Action mailed Feb. 17, 2010, 13 pgs.
U.S. Appl. No. 11/010,779, Response filed Jul. 15, 2009 to Non Final Office Action mailed Apr. 15, 2009, 16 pgs.
U.S. Appl. No. 11/010,779, Response filed Dec. 3, 2009 to Non Final Office Action mailed Apr. 15, 2009, 13 pgs.
U.S. Appl. No. 11/010,779, Restriction Requirement mailed Jan. 12, 2009, 16 pgs.
U.S. Appl. No. 11/613,319, Advisory Action mailed Jan. 19, 2010, 3 pgs.
U.S. Appl. No. 11/613,319, Final Office Action mailed Jun. 18, 2012, 11 pgs.
U.S. Appl. No. 11/613,319, Final Office Action mailed Oct. 26, 2009, 7 pgs.
U.S. Appl. No. 11/613,319, Information Disclosure Statement mailed Mar. 20, 2007, 9 pgs.
U.S. Appl. No. 11/613,319, Information Disclosure Statement mailed Sep. 3, 2010, 5 pgs.
U.S. Appl. No. 11/613,319, Information Disclosure Statement mailed Dec. 20, 2007, 6 pgs.
U.S. Appl. No. 11/613,319, Non Final Office Action mailed Mar. 13, 2009, 7 pgs.
U.S. Appl. No. 11/613,319, Non Final Office Action mailed Dec. 29, 2011, 9 pgs.
U.S. Appl. No. 11/613,319, Response filed Jan. 26, 2009 to Restriction Requirement mailed Dec. 26, 2008, 7 pgs.
U.S. Appl. No. 11/613,319, Response filed Jan. 26, 2010 to Advisory Action mailed Jan. 19, 2010, 9 pgs.
U.S. Appl. No. 11/613,319, Response filed Mar. 29, 2012 to Non Final Office Action mailed Dec. 29, 2011, 15 pgs.
U.S. Appl. No. 11/613,319, Response filed Jun. 11, 2009 to Non Final Office Action mailed Mar. 13, 2009, 8 pgs.
U.S. Appl. No. 11/613,319, Response filed Sep. 17, 2012 to Final Office Action mailed Jun. 18, 2012, 19 pgs.
U.S. Appl. No. 11/613,319, Response filed Dec. 7, 2009 to Final Office Action mailed Oct. 26, 2009, 8 pgs.
U.S. Appl. No. 11/613,319, Restriction Requirement mailed Dec. 26, 2008, 6 pgs.
U.S. Appl. No. 12/861,404, Non Final Office Action mailed May 16, 2012, 6 pgs.
U.S. Appl. No. 12/861,404, Preliminary Amendment filed Aug. 23, 2010, 6 pgs.
U.S. Appl. No. 12/976,689, Non Final Office Action mailed May 15, 2012, 7 pgs.
U.S. Appl. No. 12/976,711, Response filed Aug. 29, 2012 to Restriction Requirement mailed May 29, 2012, 4 pgs.
U.S. Appl. No. 12/976,711, Restriction Requirement mailed May 29, 2012, 6 pgs.
European Application Serial No. 04813849.9, Extended European Search Report mailed Apr. 8, 2008, 3 pgs.
European Application Serial No. 04813849.9, Office Action mailed Feb. 16, 2009, 5 pgs.
European Application Serial No. 04813849.9, Response filed Aug. 20, 2009 to Office Action mailed Feb. 16, 2009, 18 pgs.
European Application Serial No. 07862720.5, Notice of Allowance mailed Feb. 25, 2011, 6 pgs.
European Application Serial No. 07862720.5, Office Action mailed Feb. 26, 2010, 3 pgs.
European Application Serial No. 07862720.5, Response filed Sep. 1, 2010 to Office Action mailed Feb. 26, 2010, 10 pgs.
International Application Serial No. PCT/US2004/041591, Written Opinion mailed Jun. 12, 2006, 4 pgs.
International Application Serial No. PCT/US2007/025252, International Preliminary Report on Patentability mailed Jun. 23, 2009, 8 pgs.
International Application Serial No. PCT/US2007/025252, International Search Report mailed Apr. 18, 2008, 3 pgs.
International Application Serial No. PCT/US2007/025252, Written Opinion mailed Apr. 18, 2008, 7 pgs.
International Application Serial No. PCT/US2007/086468, International Preliminary Report on Patentability mailed Jun. 23, 2009, 10 pgs.
International Application Serial No. PCT/US2007/086468, International Search Report Jun. 5, 2008, 4 pgs.
International Application Serial No. PCT/US2007/086468, Written Opinion mailed Jun. 20, 2009, 9 pgs.
Bacsich, P., et al., "The Significance of the Mucoprotein Content on the Survival of Homografts of Cartilage and Cornea", vol. LXII, Part III, P.R.S.E., USA, (1946), 321-327.
Brittberg, et al., "Treatment of Deep Cartilage Defects in the Knee with Autologous Chondrocyte Transplantation", N. Engl. J. Med.: 331(14), (Oct. 6, 1994), 889-895.
Caruso, Enzo M, et al., "Repopulation of Laser-Perforated Chondroepiphyseal Matrix with Xenogenic Chondrocytes: An Experimental Model", Journal of Orthopaedic Research, vol. 14, (1996), 102-107.
Cheng, Nai-Chen, et al., "Chondrogenic Differentiation of Adipose-Derived Adult Stem Cells by a Porous Scaffold Derived from Native Articular Cartilage Extracellular Matrix", Tissue Engineering: Part A, vol. 15 No. 2, (2009), 231-244.
Cherubino, P., et al., "Autologous chondrocyte implantation using a bilayer collagen membrane: A preliminary report", Journal of Orthopaedic Surgery vol. II, No. 1, Italy, (2003), 10-15.
Cheung, H, et al., "Growth of osteoblasts on porous calcium phosphate ceramic: an in vitro model for biocompatibility study", Biomaterials vol. 10, Issue 1, (Jan. 1989), 63-67.
Davis, John Staige, "Some of the Problems of Plastic Surgery", Read before the Philadelphia Academy of Surgery, (Mar. 5, 1917), 88-94.
Davis, W. Brian, et al., "Absorption of Autogenous Cartilage Grafts in Man", British Journal of Plastic Surgery, vol. 9, (1956), 177-185.
Degroot, Jeroen, et al., "Age Related Decrease in Proteoglycan Synthesis of Human Articular Chondrocytes", The Role of Nonenzymatic Glycation Arthritis and Rheumatism, vol. 42, No. 5 (May 1999), 1003-1009.
Didier, R, et al., "Production de cartilage et d'os, au sein de greffes vivantes et mortes, chez le lapin", Comptes Rendus Hebdomadaires, (1928), 5 pp.
Feder, Joseph, et al., "The Promise of Chondral Repair Using Neocartilage", Chapter 22, (2004), 219-226.
Gu, Joseph D, et al., "True Density of Normal and Enzymatically Treated Bovine Articular Cartilage", Orthopaedic Research Laboratory, Columbia University, (1999), 642.
Hendrickson, Dean A, "Chondrocyte-Fibrin Matrix Transplants for Resurfacing Extensive Articular Cartilage Defects", Journal of Orthopaedic Research vol. 12 The Journal of Bone and Joint Surgery, Inc., (1994), 485-497.
Homminga, George N, et al., "Chondrocyte Behavior in fibrin glue in vitro", Acta Orthop Scand, vol. 64 No. 4, (1993), 441-445.
Howard, R. D., "Long-term fate and effects of exercise on sternal cartilage autografts used for repair of large osteochondral defects in horses", Am Journal Vet Res, vol. 55 No. 8, (Aug. 1994), 1158-1167.
Hunziker, E.B., et al., "Quantitative structural organization of normal adult human articular cartilage", Osteoarthritis and Cartilage 10, (2002), 564-572.
Hutchinson, John, "Observations on Bone Transplants in the Anterior Chamber of the Eye", Glasgow Medical Journal, (1949), 657-363.
Imbert, Leon, et al., "Recherches sur les greffes cartilagineuses hetero-plastiques", Revue de Chirurgie, Paraissant tous les mois, (1916), 20 pp.
Jeffries, David J, et al., "Cartilage Regeneration Following Septal Surgery in Young Rabbits", The Journal of Laryngology and Otology vol. 98, (Jun. 1984), 577-583.
Kawamura, et al., "Human Fibrin Is a Physiologic Delivery System for Bone Morphogenetic Protein", Clinical Orthopaedics and Related Research, (Oct. 1988), 302-310.
Kim, Myung Ku, et al., "Autologous chondrocyte implantation in the knee using fibrin", Knee Surg Sports Traumatol Arthrosc vol. 18, (2010), 528-534.

Kirilak, Yaow Anuj, et al., "Fibrin Sealant Promotes Migration and Proliferation of Human Articular Chondrocytes: Possible Involvement of Thrombin and Protease-activated receptors", International Journal of Molecular Medicine vol. 17, (2006), 551-558.

Lapchinsky, A G, et al., "Instrument for Shredding Cartilage in Plastic Surgeries", New Surgical Machines and Instruments and their usage, No. 4, Moscow, (1960), 209-213.

Longacre, J J, et al., "Further Observations of the Behavior of Autogeneous Split-Rib Grafts in Reconstruction of Extensive Defencts of the Cranium and Face", Plastic and Reconstructive Surgery, vol. 20 No. 4, Read at the Meeting of the American Association of Plastic Surgeons, Skytop, PA, (Oct. 1957), 281-296.

Mannheim, A, "Free Autoploastic Cartilage transplantation—Uber freie autoplastische Knorpeltransplantation", Arch. F klin Chir, (1926), 668-672.

Marmotti, A, et al., "One-step osteochondral repair with cartilage fragments in a composite scaffold", Knee Surg Sports Traumatol Arthrosc, (Feb. 21, 2012), 12 pp.

Marvin, H M, "The Value of the Xanthine Diuretics in Congestive Heart Failure", The Journal of the American Medical Association, vol. 87, No. 25, Abstract only, (Dec. 18, 1926), 2131-2132.

McDermott, et al., "Fresh small fragment osteochondral allografts", Clinical Orthopaedics and Related Research, No. 197, (1985), 96-102.

McKibbin, B, et al., "The Dual Nature of Epiphysical Cartilage", Department of Orthopaedics, vol. 49B, No. 2, (May 1967), 351-361.

Medawar, P. B., "Immunity to Homologous Grafted Skin. III. The Fate of Skin Homografts Transplanted to the Brain, to Subcutaneous Tissue, and to the Anterior Chamber of the Eye", Department of Zoology Immunity to Homologous Grafted Skin, (Dec. 8, 1947), 58-69.

Morales, T I, "Review Chondrocyte moves: clever strategies?", Osteoarthritis and Cartilage vol. 15 No. 8 International Cartilage Repair Society, (2007), 861-871.

Munirah, S, et al., "Articular Cartilage Restoration in load-bearing osteochondral defects by implantation of autologous chondrocyte-fibrin constructs", The Journal of Bone and Joint Surgery, vol. 89-B, No. 8, An Experimental Study in Sheep, (Aug. 2007), 1099-1109.

Namba, Robert S., "Spontaneous Repair of Superficial Defects in Articular Cartilage in a Fetal Lamb Model", Journal of Bone and Joint Surgery, Inc., (1998), 4-10.

Nehrer, S, et al., "Three-year Clinical Outcome after chondrocyte transplantation using a hyaluronan matrix for cartilage repair", European Journal of Radiology vol. 57, (2006), 3-8.

Nehrer, Stefan, et al., "Treatment of Articular Cartilage Defects", Investigative Radiology, vol. 35, No. 10, (2000), 639-646.

Peretti, Giuseppe M, et al., "A biomechanical Analysis of an Engineered Cell-Scaffold Implant for Cartilage Repair", Animals of Plastic Surgery vol. 46 No. 5, (May 2001), 533-537.

Peretti, Giuseppe M, et al., "Cell-Based Tissue-Engineered Allogenic Implant for Cartilage Repair", Tissue Engineering, vol. 6 No. 5, (2000), 567-576.

Pierce, Angela, et al., "Surgicel: macrophage processing of the fibrous component", International Journal of Oral Maxillofac Surgery vol. 16, (1987), 338-345.

Polettini, B, "Experimental Grafts of Cartilage and bone", The Journal of the American Medical Association, vol. 80, Abstract, (1923), 360-361.

Polettini, Bruno, "Su neoformazioni carilaginee ed ossee determinate da innesti di frammenti di cartilagine e d'osso fissati", (1922), 179-192.

Roemhildt, Maria L, et al., "Material Properties of Articular Cartilage in the Rabbit Tibial Plateau", J Biomech vol. 39 No. 12, (2006), 2331-2337.

Schwam, B, "Human Amniotic Membrane Transplantation for the Treatment of Ocular Surface Disease", [Online]. Retrieved from the Internet: <URL: http://www.dcmsonline.org/jax-medicine/2002journals/augsept2002/amniotic.htm>, (2002), 7 pgs.

Seliktar, Dror, "Nature's Healing Matrix", Technion Focus, (May 2006), 1.

Sengupta, S, et al., "The Fate of Transplants of Articular Cartilage in the Rabbit", JBJS, vol. 56B, No. 1, (1974), 167-177.

Shands, A R, "The Regeneration of Hyaline Cartilage in Joints", Archives of Surgery, vol. 22, (1931), 137-178.

Silverman, Ronald P, et al., "Adhesion of Tissue-Engineered Cartilage to Native Cartilage", Plastic and Reconstructive Surgery, vol. 105, No. 4, (Apr. 2000), 1393-1398.

Sin, Y M, et al., "Studies of the Mechanism of Cartilage Degradation", Journal of Pathology, vol. 142, (1984), 23-30.

Sittinger, M, et al., "Engineering of cartilage tissue using bioresorbable polymer carriers in perfusion culture", Biomaterials 15(6), (1994), 451-6.

Van Susante, Job L.C., et al., "Resurfacing potential of heterologous chondrocytes suspended in fibrin glue in large full-thickness defects of femoral articular cartilage: an experimental study in the goat", Biomaterials vol. 20, (1999), 1167-1175.

Verwoerd, C.D.A., et al., "Stress and Woundhealing of the Cartilaginous Nasal Septum", Acta Otolaryngol (Stockh) vol. 107, (1989), 441-445.

Verwoerd, C.D.A., et al., "Wound Healing of Autologous Implants in the Nasal Septal Cartilage", Department of Otorhinolaryngology and Pathology, ORL vol. 53, (1991), 310-314.

Wikipedia, "Alpha-2-Macroglobulin", 8 pp.

Wilflingseder, Paul, "Cancellous Bone Grafts", S.A. Medical Journal, (Dec. 14, 1957), 1267-1271.

Wilflingseder, Paul, "Treatment of Mandibular Facial Dysostosis", S.A. Medical Journal, (Dec. 21, 1957), 1296-1298.

Williamson, Amanda K, et al., "Compressive Properties and Function-composition relationships of developing bovine articular cartilage", Journal of Orthopaedic Research vol. 19, (2001), 1113-1121.

U.S. Appl. No. 12/063,291, Notice of Allowance mailed Mar. 4, 2013, 7 pgs.

International Application Serial No. PCT/US08/60078, International Search Report mailed Sep. 3, 2008, 3 pgs.

Adibi, Siamak A, et al., "Removal of Glycylglutamine from Plasma by Individual Tissues: Mechanism and Impact on Amino Acid Fluxes in Postabsorption and Starvation", The Journal of Nutrition, Symposium: Nutritional and Hormonal Regulation of Amino Acid Metabolism, (1993), 325-331.

Brighton, Carl T, et al., "In Vitro Rabbit Articular Cartilage Organ Model II. 35S Incorporation in Various Oxygen Tensions", Arthritis and Rheumatism vol. 17, No. 3, (May 1974), 245-252.

Butler, M, et al., "Nutritional aspects of the growth of animal cells in culture", Journal of Biotechnology 12, (1989), 97-110.

Butler, Michael, et al., "Adaptation of mammalian cells to non-ammoniagenic media", Cytotechnology 15, (1994), 87-94.

Chesterman, P. J., et al., "Cartilage as a Homograft", The Journal of Bone and Joint Surgery. Proceedings and reports of councils and associations, (1968), 878.

Christie, A, et al., "Glutamine-based dipeptides are unilized in mammalian cell culture by extracellular hydrolysis catalyzed by a specific peptidase", Journal of Biotechnology 37, (1994), 277-290.

Frisbie, David D, et al., "In Vivo Evaluation of Autologous Cartilage Fragment-Loaded Scaffolds Implanted Into Equine Articular Defects and Compared With Autologous Chondrocyte Implantation", The American Journal of Sports Medicine 37, (Nov. 24, 2009), 71S-80S.

Glacken, Michael W, "Catabolic Control of Mammalian Cell Culture", Biotechnology vol. 6, (Sep. 1998), 1041-1050.

Hammarqvist, Folke, et al., "Alanyl-glutamine Counteracts the Depletion of Free Glutamine and the Postoperative Decline in Protein Synthesis in Skeletal Muscle", Ann. Surg, (Nov. 1990), 637-644.

Hassell, T, et al., "Growth Inhibition in Animal Cell Culture: The Effect of Lactate and Ammonia", Applied Biochemistry and Biotechnology, vol. 30, (1991), 29-41.

McCormick, F., "Minced Articular Cartilage—Basic Science, Surgical Technique, and Clinical Application", Sports Med. Arthrosc. Rev., vol. 16, No. 4, (Dec. 2008), 217-220.

McIlwraith, C W, et al., "In-Vivo Evaluation of a One-Step Autologous Cartilage Resurfacing Technique (CAIS)—Comparison of Three Different Scaffolds", 6th Symposium of the International Cartilage Repair Society, (Jan. 2006), p. 3-6.

Minamoto, Yoshiki, et al., "Development of a serum-free and heat-sterilizable medium and continuous high-density cell culture", Cytotechnology, vol. 5, (1991), S35-S51.

Newland, M, et al., "Hybridoma growth limitations: The roles of energy metabolism and ammonia production", Cytotechnology, vol. 3, (1990), 215-229.

Reitzer, Lawrence J, et al., "Evidence that Glutamine, Not Sugar, is the Major Energy Source for Cultured HeLa Cells", The Journal of Biological Chemistry, vol. 254, No. 8, (Apr. 1979), 2669-2676.

Roth, E, et al., "Influence of Two Glutamine-Containing Dipeptides on Growth of Mammalian Cells", In Vitro Cellular & Developmental Biology, vol. 24, No. 7, (Jul. 1988), 696-698.

Zielke, Ronald H, et al., "Glutamine: a major energy source for mammalian cells", Federation Proceedings, vol. 43, No. 1, (Jan. 1984), 121-125.

U.S. Appl. No. 10/874,402, Final Office Action mailed Feb. 22, 2011, 10 pgs.

U.S. Appl. No. 10/874,402, Final Office Action mailed Apr. 17, 2009, 17 pgs.

U.S. Appl. No. 10/874,402, Final Office Action mailed Apr. 19, 2010, 13 pgs.

U.S. Appl. No. 10/874,402, Non Final Office Action mailed Apr. 10, 2008, 9 pgs.

U.S. Appl. No. 10/874,402, Non Final Office Action mailed Sep. 22, 2010, 11 pgs.

U.S. Appl. No. 10/874,402, Non Final Office Action mailed Oct. 27, 2009, 15 pgs.

U.S. Appl. No. 11/413,419, Final Office Action mailed Aug. 25, 2009, 13 pgs.

U.S. Appl. No. 11/413,419, Non Final Office Action mailed Jun. 26, 2008, 12 pgs.

U.S. Appl. No. 11/613,456, Advisory Action mailed Aug. 11, 2009, 3 pgs.

U.S. Appl. No. 11/613,456, Final Office Action mailed Jun. 4, 2009, 7 pgs.

U.S. Appl. No. 11/613,456, Non Final Office Action mailed Jan. 23, 2009, 6 pgs.

U.S. Appl. No. 11/613,456, Non Final Office Action mailed Sep. 11, 2009, 5 pgs.

U.S. Appl. No. 11/613,456, Notice of Allowance mailed Jan. 19, 2010, 5 pgs.

U.S. Appl. No. 11/613,456, Response filed Apr. 3, 2009 to Non Final Office Action mailed Jan. 23, 2009, 8 pgs.

U.S. Appl. No. 11/613,456, Response filed Aug. 4, 2009 to Final Office Action mailed Jun. 4, 2009, 9 pgs.

U.S. Appl. No. 11/613,456, Response filed Nov. 6, 2008 to Restriction Requirement mailed Oct. 7, 2008, 7 pgs.

U.S. Appl. No. 11/613,456, Response filed Dec. 7, 2009 to Non Final Office Action mailed Sep. 11, 2009, 9 pgs.

U.S. Appl. No. 11/613,456, Restriction Requirement mailed Oct. 7, 2008, 6 pgs.

U.S. Appl. No. 12/063,291, Final Office Action mailed Mar. 15, 2012, 10 pgs.

U.S. Appl. No. 12/063,291, Final Office Action mailed Mar. 22, 2011, 8 pgs.

U.S. Appl. No. 12/063,291, Non Final Office Action mailed Sep. 15, 2010, 6 pgs.

U.S. Appl. No. 12/063,291, Notice of Allowance mailed Aug. 8, 2012, 9 pgs.

U.S. Appl. No. 12/063,291, Notice of Allowance mailed Oct. 11, 2012, 8 pgs.

U.S. Appl. No. 12/063,291, Preliminary Amendment filed Feb. 8, 2008, 9 pgs.

U.S. Appl. No. 12/063,291, Response filed Jan. 21, 2011 to Non Final Office Action mailed Sep. 15, 2010, 12 pgs.

U.S. Appl. No. 12/063,291, Response filed Jul. 16, 2012 to Final Office Action mailed Mar. 15, 2012, 13 pgs.

U.S. Appl. No. 12/063,291, Response filed Sep. 22, 2011 to Final Office Action mailed Mar. 22, 2011, 10 pgs.

U.S. Appl. No. 12/101,553, Response filed Aug. 15, 2011 to Restriction Requirement mailed Jul. 13, 2011, 11 pgs.

U.S. Appl. No. 12/101,553, Final Office Action mailed Sep. 14, 2012, 9 pgs.

U.S. Appl. No. 12/101,553, Final Office Action mailed Dec. 28, 2012, 9 pgs.

U.S. Appl. No. 12/101,553, Non Final Office Action mailed Nov. 9, 2011, 8 pgs.

U.S. Appl. No. 12/101,553, Response filed May 9, 2012 to Non Final Office Action mailed Nov. 9, 2011, 14 pgs.

U.S. Appl. No. 12/101,553, Restriction Requirement mailed Jul. 13, 2011, 17 pgs.

U.S. Appl. No. 12/751,230, Non Final Office Action mailed Sep. 1, 2010, 9 pgs.

U.S. Appl. No. 12/751,230, Preliminary Amendment filed Mar. 31, 2010, 7 pgs.

U.S. Appl. No. 12/751,230, Response filed Jul. 30, 2010 to Restriction Requirement mailed Jul. 21, 2010, 5 pgs.

U.S. Appl. No. 12/751,230, Restriction Requirement mailed Jul. 21, 2010, 53 pgs.

U.S. Appl. No. 12/976,711, Examiner Interview Summary mailed Nov. 15, 2012, 3 pgs.

U.S. Appl. No. 12/976,711, Non Final Office Action mailed Dec. 12, 2012, 9 pgs.

U.S. Appl. No. 12/976,711, Response filed Dec. 3, 2012 to Restriction Requirement mailed Oct. 14, 2012, 6 pgs.

U.S. Appl. No. 12/976,711, Restriction Requirement mailed Oct. 4, 2012, 6 pgs.

U.S. Appl. No. 13/327,238, Non Final Office Action mailed Jan. 2, 2013, 8 pgs.

U.S. Appl. No. 13/327,238, Preliminary Amendment filed Jun. 1, 2012, 6 pgs.

U.S. Appl. No. 13/327,238, Response filed Dec. 7, 2012 to Restriction Requirement mailed Sep. 7, 2012, 6 pgs.

U.S. Appl. No. 13/327,238, Restriction Requirement mailed Sep. 7, 2012, 11 pgs.

U.S. Appl. No. 13/327,265, Final Office Action mailed Jan. 31, 2013, 8 pgs.

U.S. Appl. No. 13/327,265, Non Final Office Action mailed Apr. 2, 2012, 10 pgs.

U.S. Appl. No. 13/327,265, Response filed Sep. 4, 2012 to Non Final Office Action mailed Apr. 2, 2012, 7 pgs.

U.S. Appl. No. 13/327,286, Non Final Office Action mailed Feb. 7, 2013, 9 pgs.

U.S. Appl. No. 13/327,286, Preliminary Amendment filed Jun. 1, 2012, 7 pgs.

Application Serial No. 2008240191, First Examination Report mailed Sep. 21, 2012.

Australian Application Serial No. 2006282754, Office Action mailed Nov. 8, 2011, 3 pgs.

"Combine", Merriam-Webster Online Dictionary, [Online] Retrieved From Internet: <http://www.merriam-webster.com/dictionary/combine>, (Jul. 13, 2011), 2 pgs.

European Application Serial No. 11154746.9, Response filed Dec. 14, 2012 to Office Action mailed Nov. 15, 2012, 4 pgs.

European Application Serial No. 11154746.9, Search Report mailed May 23, 2011, 4 pgs.

European Application Serial No. 11154747.7, Response filed Dec. 14, 2012 to Office Action mailed Nov. 21, 2012, 4 pgs.

European Application Serial No. 11154747.7, Search Report mailed May 23, 2011, 4 pgs.

European Application Serial No. 11154748.5, Search Report mailed May 24, 2011, 4 pgs.

International Application Serial No. PCT/US2008/60078, International Search Report mailed Sep. 3, 2008, 1 pg.

International Application Serial No. PCT/US2006/33687, International Preliminary Report on Patentability mailed Feb. 26, 2008, 7 pgs.

International Application Serial No. PCT/US2006/33687, Written Opinion mailed Aug. 8, 2007, 6 pgs.

Japanese Application Serial No. 2008-528250, Office Action mailed Jun. 22, 2012, 5 pgs.

Japanese Application Serial No. 2008-528250, Response filed Nov. 22, 2012 to Office Action mailed Jun. 22, 2012, 9 pgs.

"Morsel", Merriam-Webster Online Dictionary, [Online] Retrieved From Internet: <http://www.merriam-webster.com/dictionary/morsel>, (Jul. 13, 2011), 2 pgs.

"Pulverize", Merriam-Webster Online Dictionary, [Online] Retrieved From Internet: <http://www.merriam-webster.com/dictionary/pulverize>, (Jul. 13, 2011), 2 pgs.

Adkisson, H. Davis, et al., "The Potential of Human Allogeneic Juvenile Chondrocytes for Restoration of Articular Cartilage", The American Journal of Medicine vol. 38, (Apr. 27, 2010), 1324-1333.

Adkisson, H.D.IV, et al., "In Vitro Generation of Scaffold Independent Neocartilage", Clin Ortho Rel Res, No. 391S, (2001), S280-S294.

Akens, M K, et al., "In Vitro Studies of a Photo-oxidized Bovine Articular Cartlage", Journal of Veterinary Medicine, vol. 49, Blackwell Wissenschafts-Verlag, Berlin, (2002), 39-45.

Albrecht, F, "Closure of Joint Cartilage Defects Using Cartilage Fragments and Fibrin Glue", English Abstract of German Article, Fortschr Med, vol. 101, No. 37, (1983), 1650-2.

Alfredson, Hakan, et al., "Superior results with continuous passive motion compared to active motion after periosteal transplantation", vol. 7, Knee Surg sports Trautnatol Arthrosc, Springer-Verlag, Germany, (1999), 232-238.

Alston, et al., "New method to prepare autologous fibrin glue on demand", Translational Research vol. 149, (2007), 187-195.

Augenstein, D C, et al., "Effect of Shear on the Death of Two Strains of Mammalian Tissue Cells", vol. XIII, Biotechnology and Bioengineering, USA, (1971), 409-418.

Aulthouse, Amy Lynn, et al., "Expression of the Human Chondrocyte Phenotype in Vitro", vol. 25, No. 7, In Vitro Cellular & Developmental Biology, USA, (1989), 659-668.

Azizkhan, et al., "Chondrocytes contain a growth factor that is localized in the nucleus and is associated with chomatin", Proc. Natl. Acad. Sci., vol. 77, No. 5, (1980), 2762-2766.

Bartlett, W, et al., "Autologous chondrocyte implantation at the knee using a bilayer collagen membrane with bone graft", vol. 87-B, The Journal of Bone & Joint Surgery [Br], London, (2005), 330-332.

Bartlett, W, et al., "Autologous chondrocyte implantation versus matrix-induced autologous chondrocyte implantation for osteochondral defects of the knee", vol. 87-B, No. 5, The Journal of Bone & Joint Surgery [Br], London, (2005), 640-645.

Bassleer, C, et al., "Human Chondrocytes in Tridimensional Culture", vol. 22, No. 3, Pl. 1, in Vitro Cellular & Developmental Biology, UK, (1986), 113-119.

Behrens, Peter, et al., "Matrix-associated autologous chondrocyte trnasplantationlimplantation (MACTIMACI)-5-year follow-up", vol. 13, The Knee, Elsevier, UK, (2006), 194-202.

Ben-Zeev, A, et al., "Protein synthesis requires cell-surface contact while nuclear events respond to cell shape in anchorage-dependent fibroblasts", Cell, vol. 21., (1980), 365-372.

Binette, F, et al., "Tenninally Redifferentiated Human Articular Chondrocytes Express Hyaline Cartilage Markers without Hypertrophy", Genzyrne Tissue Repair, 43rd Annual Meeting, Orthopaedic Research Society, USA, (1997), 520 pgs.

Black, J., "Biological Performance of Tantalum", Clinical Materials, vol. 16., (1994), 167-173.

Bobyn, J D, et al., "Effect of pore size on the peel strength of attachment of fibrous tissue to porous-surfaced implants", J. Biomed. Mater. Res., vol. 16., (1982), 571-584.

Bobyn, JD, et al., "Characteristics of bone ingrowth and interface mechanics of a new porous tantalum biomaterial", J. Bone Joint Surg Br., 81, (1999), 907-914.

Bobyn, JD, et al., "Tissue response to porous tantalum acetabular cups", a canine model. J. Arthroplasty, 14, (1999), 347-54.

Bodo, G, et al., "Arthroscopic Autologous Osteochondral Mosiacplasty for the Treatment of Sybchondral Cystic Lesion in the Medical Femoral Condyle in a Horse", Acta Veterinaria Hungarica, vol. 48 Vo. 3, (2000), 343-354.

Boumediene, et al., "Modulation of rabbit articular chondrocyte (RAC) proliferation by TGF-B isoforms", Cell Prolif., vol. 28, (1995), 221-234.

Braun, A, et al., "The Use of Fibrin Adhesive in Fixation of Osteochondral Fragments", Abstract only, Canadian Orthopaedic Research Society, 215-216.

Breadon, G E, et al., "Autografts of Uncrushed and Crushed Bone and Cartilage", Bone and Cartilage Autografts, vol. 108, (1979), 75-80.

Brighton, et al., "Articular Cartilage Preservation and Storage", Arthritis and Rheumatism 22(10), (1979), 1093-1101.

Brodkin, H A, "Diced Cartilage for Chest Wall Defects", vol. 28, No. 1, (1954), 97-102.

Brown, B L, et al., "Transplantation of Fresh Allografts (Homografts) of Crushed and Uncrushed Cartilage and Bone: A 1-Year Analysis in Rabbits", The Laryngoscope, vol. 90, (1980), 1521-1532.

Bruns, J, et al., "Autologous Perichondrial Transplantation for the Repair of Experimentally Induced Cartilage Defects in the Sheep Knee-Two Glueing Techniques", Orthopedic Surgery Maxilofacial Surgery, Fibrin Sealing in Surgical and Nonsurgical Fields, Springer, Berlin, Heidelber, (Oct. 27, 1994), 50-60.

Bruns, J, et al., "Long-Term Follow up Results after Gluing Osteochondral Fragments in Patients with Osteochondrosis Dissecans", Langenbecks Arch Chir, vol. 378, (1993), 160-166.

Bujia, et al., "Synthesis of human cartilage using organotypic cell culture", ORL, vol. 55, (1993), 347-351.

Bujia, J, et al., "Culture and Cryopreservation of Chondrocytes from Human Cartilage: Relevance for Cartilage Allografting in Otolaryngology", ORL, (1992), 80-84.

Bujia, J, "Determination of the Viability of Crushed Cartilage Grafts: Clinical Implications for Wound Healing in Nasal Surgery", Ann Plast Surg, vol. 32, (1994), 261-265.

Bujia, J, et al., "Effect of Growth Factors on Cell Proliferation by Human Nasal Septal Chondrocytes Cultured in Monolayer", Acta Otolaryngol, vol. 114, Scandinavian University Press, Sweden, (1994), 539-543.

Calandruccio, et al., "Proliferation, Regeneration, and Repair of Articular Cartilage of Immature Animals", J. Bone Joint Surg, vol. 44-A, No. 3, (1962), 431-455.

Chang, et al., "Cartilage-Derived Morphogenetic Proteins", J. Biol. Chem., 269, (1994), 28227-28234.

Chawla, K, et al., "Short-term retention of labeled chondrocyte subpopulations in stratified tissue-engineered cartilaginous constructs implanted in vivo in mini-pigs", Tissue Engineering vol. 13, No. 7, (2007), 1525-1538.

Cherry, R S, et al., "Hydrodynamic effects on cells in agitated tissue culture reactors", Bioprocess Engineering, vol. I, Springer-Verlag, USA, (1986), 29-41.

Cherry, Robert S, et al., "Physical Mechanisms of Cell Damage in Microcarrier Cell Culture Bioreactors", Biotechnology and Bioengineering, vol. 32, John Wiley & Sons, Inc., USA, (1988), 1001-1014.

Cherry, Robert S, et al., "Understanding and Controlling Fluid-Mechanical Injury of Animal Cells in Bioreactors", Animal Cell Biotechnology, vol. 4, Academic Press Limited, USA, (1990), 71-121.

Chesterman, P J, et al., "Homotransplantation of Articular Cartilage and Isolated Chondrocytes, An Experimental Study in Rabbits", JBJS, (1968), 184-197.

Choi, Ye Chin, et al., "Effect of Platelet Lysate on Growth and Sulfated Glycosaminoglycan Synthesis in Articular Chondrocyte Cultures", Arthritis and Rheumatism, vol. 22, No. 2, USA, (1980), 220-224.

Christel, P, et al., "Osteochondral Grafting using the Mosaicplasty Technique", [Online] Retrived from the internet Dec. 16, 2008: <www.maitrise-orthop.com/corpusmaitri/orthopaedic/mo76_mosaicplasty/index.shtm>, 20 pgs.

Cooke, M E, et al., "Structured Three-dimensional co-culture of mesenchymal stem cells with chondrocyts promotes chondrogenic differentiation without hypertrophy", 1-19.

Coutts, Richard D, et al., "Rib Perichondrial Autografts in Full-Thickness Articular Cartilage Defects in Rabbits", Clinic Orthopaedics and Related Research, No. 275, USA, (1989), 263-273.

Craigmyle, M.B.L., "An Autoradiographic and Histochemical Study of Long-term Cartilage Grafts in the Rabbit", J of Anatomy, vol. 92, part 3, (1954), 467-473.

Craigmyle, M.B.L., "Cellular Survival in Long-Term Cartilage Grafts in the Rabbit", Transplantation Bulletin, vol. 5, No. 1, (1958), 123.

Croughan, Matthew Shane, et al., "Hydrodynamic Effects on Animal Cells Grown in Microcarrier Cultures", Biotechnology and Bioengineering, vol. XXIX, John Wiley & Sons, Inc., USA, (1987), 130-141.

Decher, H, "Reduction of Radical Cavities by Means of Homologous Cartilage Chips", Larying. Rhinol. Otol., vol. 64, (1985), 423-426.

Delbruck, Axel, et al., "In-Vitro Culture of Human Chondrocytes from Adult Subjects", Connective Tissue Research, Gordon and Breach, Science Publishers, Inc., USA, (1986), 155-172.

Dewey, Jr, C F, et al., "The Dynamic Response of Vascular Endothelial Cells to Fluid Shear Stress", Journal of Biomechnical Engineering, vol. 103, USA, (1981), 177-185.

Didier, R, et al., "The production of cartilage and bone grafts in living and dead rabbits", Compt. rend. Soc de bioi, vol. 98, (1928), 443-445.

Dogterom, A A, et al., "Matrix depletion of young and old human articular cartilage by cultured autologous synovium fragments; a chondrocyte-independent effect", Rheumatology International, vol. 5, Springer-Verlag, UK, (1985), 169-173.

Dowthwaite, Gary P, et al., "The surface of articular cartilage contains a progenitor cell population", Journal of Cell Science vol. 117, The Company of Biologists, 2004 UK, (2004), 889-897.

Drobnic, M. Md, et al., "Comparison of four techniques for the fixation of a collagen scaffold in the human cadaveric knee", Osteoarthritis and Cartilage, vol., 14 Elsevier Ltd., UK, (2006), 337-344.

Dupertuis, S M, "Growth of Young Human Autogenous Cartilage Grafts", Plast Reconstr Surg, vol. 5, No. 6, (1946), 486-93.

Eberlin, J L, et al., "Osteocartilagenous Reconstruction, Plastic Surgery Nerve Repair Burns, Fibrin Sealing in Surgical and Nonsurgical Fields", vol. 3, Springer-Verlag, Berlin, Heidelberg, (1995), 20-24.

Egkher, E, et al., "Indications and Limits of Fibrin Adhesive Applied to Traumatological Patients", Traumatology and Orthopaedics, vol. 7, Springer-Verlag, Berlin Heidelberg, (1986), 144-151.

Elima, Kati, et al., "Expression of mRNAs for collagens and other matrix components in dedifferentiating and redifferentiating human chondrocytes in culture", FEBS Letters, vol. 258 No. 2, Elsevier Science Publishers B.V. (Biomedical Division), UK, (1989), 195-198.

Erikson, U, et al., "A Roentgenological Method for the Determination of Renal Blood Flow", English Abstract Only. A preliminary report, Acta Soc Med Ups, vol. 70, No. 3, (1965), 213-6.

Evans, C H, et al., "Experimental Arthritis Induced by Intraarticular Injection of Allogenic Cartilageinous Particles into Rabbit Knees", Arthritis and Rheumatism, vol. 27, No. 2, (1984), 200-207.

Evans, Robin C, et al., "Solute diffusivity correlates with mechanical properties and matrix density of compressed articular cartilage", Archives of Biochemistry and Biophysics, vol. 442, Elsevier, UK, (2005), 1-10.

Farmer, S R, et al., "Altered Translatability of Messenger RNA from Suspended Anchorage-Dependent Fibroblasts", Reversal upon Cell Attachment to a Surface, Cell, vol. 15., (1978), 627-637.

Farrior, R T, "Implant Materials in Restoration of Facial Contour", Laryngoscope, vol. 76, No. 5, (1966), 934-54.

Feder, J, "Tissue Engineering in Musculoskeletal Clinical Practice: The Promise of Chondral Repair Using Neocartilage", Am. Acad. Orthop. Surg., Chapter 22., (2004), 219-226.

Feder, Joseph, et al., "The Large-Scale Cultivation of Mammalian Cells", Scientific American, Inc USA, (1983), 36-43.

Feldman, M D, et al., "Compatibility of Autologous Fibrin Adhesive With Implant Materials", Arch Otolaryngol Head Neck Surg, vol. 114, (1988), 182-185.

Folkman, J, et al., "Role of cell shape in growth control", Nature, vol. 273., (1978), 345-349.

Frangos, John, et al., "Flow Effects on Prostacyclin Production by Cultured Human Endothelial Cells", Science, vol. 227, Texas, USA, (1985), 1477-1479.

Freed, L E, et al., "Neocartilage formation in virtro and invivo using cells cultured on synthetic biodegradable polymers", J. Biomed. Mater. Res. vol. 27 (1), (1993), 11-23.

Freed, L. E, et al., "Cartilage Tissue Engineering Based on Cell-Polymer Constructs", Tissue Engineering of Cartilage, CRC Press, Inc., USA, (1995), 1788-1806.

Freed, L. E, et al., "Composition of Cell-Polymer Cartilage Implants", Biotechnology and Bioengineering, vol. 43, John Wiley & Sons, Inc., USA, (1994), 605-614.

Freed, L. E, et al., "Cultivation of Cell-Polymer Cartilage Implants in Bioreactors", Journal of Cellular Biochemistry, vol. 51, Wiley-Liss, Inc., USA, (1993), 257-264.

Freed, L. E, et al., "Cultivation of Cell-Polymer Tissue Constructs in Simulated Microgravity", Biotechnology and Bioengineering, vol. 46, John Wiley & Sons, Inc., USA, (1995), 306-313.

Freed, Lisa E, et al., "Tissue engineering of cartilage in space", Proc. Natl. Acad. Sci., vol. 94, The National Academy of Sciences, USA, (1997), 13885-13890.

Fry, Donald, "Acutte Vascular Endothelial Changes Associated with Increased Blood Velocity Gradients,", Journal of the American Heart Association, vol. XXII, American Heart Association, USA, (1968), 165-197.

Furukawa, T, et al., "Biochemical Studies on Repair Cartilage Resurfacing Experimental Defects in the Rabbitt Knee", J Bone Joint Surg Am, vol. 62, No. 1, (1980), 79-89.

Fu?, M, et al., "Characteristics of human chondrocytes, osteoblasts and fibroblasts seeded onto a type I/II collagen sponge under different culture conditions", Annals of Anatomy, vol. 182, Urban & Fischer Verlag, Germany, (2000), 303-310.

Galera, et al., "Effect of transforming growth factor-B1 (TGF-B1) on matrix synthesis by monolayer cultures of rabbit chondrocytes during the dedifferentiating process", Experimental Cell Research, vol. 200, (1992), 379-392.

Gaudernak, T, et al., "Clinical Experiences Using Fibrin Sealant in the Treatment of Osteochondral Fractures, Fibrin Sealant in Operative Medicine", Traumatology and Orthopaedics, vol. 7, Springer-Verlag, Berlin, Heidelberg, (1986), 91-102.

Gelse, K, et al., "Paracrine Effect of Transplanted Rob Chondrocyte Spheroids Supports Formation of Secondary Cartilage Repair Tissue", J Ortho Res, vol. 27, (2009), 1216-1225.

Gerngross, H, et al., "Experimental Studies on the Influence of Fibrin Adhesive, Factor Xiii, and Calcitonin on the Incorporation and Remodeling of Autologous Bone Grafts", Arch Orthop Trauma Surg, vol. 106, (1986), 23, 31.

Gersdorff, M.C.H., et al., ""How I Do It" —Otology and Neurotology. A Specific Issue and Its Solution. A New Procedure for Bone Reconstruction in OTO-Microsurgery: A Mixture of Bone Dust and Fibrinogen Adhesive", Laryngoscope, vol. 95, (1985), 1278-1280.

Ghadially, J A, et al., "Evidence of Cartilage Flow in Deep Defects in Articular Cartilage", Virchows Arch B Cell Path, vol. 18, (1975), 193-204.

Ghadially, J A, et al., "Long-Term Results of Deep Defects in Articular Cartilage", Virchows Arch B. Cell Path, vol. 25, (1977), 125-136.

Gibble, et al., "Fibrin glue: the perfect operative sealant", Transfusion, 1990, vol. 30, No. 8., 741-747.

Gille, J, et al., "Migration pattern, morphology and viability of cells suspended in or sealed with fibrin glue: A histomorphologic study", Tissue and Cell, Vo. 37, Elsevier, UK, (2005), 339-348.

Girotto, Davide, et al., "Tissue-specific gene expression in chondrocytes grown on three-dimensional hyaluronic acid scaffolds", Biomaterials, vol. 24, Elsevier, UK, (2003), 3265-3275.

Gooch, K J, et al., "Effects of Mixing Intensity on Tissue-Engineered Cartilage", Biotechnology and Bioengineering, vol. 72, No. 4, John Wiley & Sons, Inc., USA, (2001), 402-407.

Gooding, C R, et al., "A Prospective, Randomised Study Compairing Two Techniques of Autologous Chondrocyte Implantation for Osteochondral Defects in the Knee: Periosteum Covered Versus Type I/III Collagen Covered", Abstract Only, Knee, vol. 13, No. 3, (2006), 203-10.

Greco, F, et al., "Experimental Investigation into Reparative Osteogenesis With Fibrin Adhesive", Arch Orthop Trauma Surg, vol. 107, (1988), 99-104.

Guilak, F, et al., "Functional tissue engineering: the role of biomechanics in articular cartilage repair", Clin Orthop Relat Res, vol. 391S., (2001), 295-305.

Haart, et al., "Optimization of chondrocyte expansion in culture", Acta Orthop Scand, vol. 70, No. 1, (1999), 55-61.

Hacking, S A, et al., "Fibrous tissue ingrowth and attachment to porous tantalum", J. Biomed. Mater. Res., vol. 52, No. 4., (2000), 631-638.
Hamra, S T, "Crushed Cartilage Grafts over Alar Dome Reduction in Open Rhinoplasty", Plast Reconstr Surg, vol. 92, No. 2, (1993), 352-6.
Han, et al., "Scaffold-free Grafts for Articular Cartilage Defects", Clin Orthop Relat Res. vol. 466, (2008), 1912-1920.
Hangody, L, et al., "Autologous Osteochondral Mosaicplasty for the Treatment of Full-Thickness Defects of Weight-Bearing Joints: Ten Years of Experimental and Clinical Experience", JBJS, vol. 85, (2003), 25-32.
Hangody, L, et al., "Mosaicplasty for the Treatment of Articular Defects of the Knee and Ankle", Clin Orthopaedics and Rel Res, No. 391S, (2001), S328-S336.
Harbin, M, et al., "Autogenous Free Cartilage Transplanted into Joints", Archives of Surgery, vol. 20, No. 6, (1930), 885-896.
Harrison, et al., "Osteogenin promotes reexpression of cartilage phenotype by dedifferentiated articular chondrocytes in serum-free medium", Experimental Cell Research, vol. 192, (1991), 340-345.
Harrison, et al., "Transforming growth factor-beta: Its effect on phenotype reexpression by dedifferentiated chondrocytes in the presence and absence of osteogenin", In Vitro Cell Dev. Biol., vol. 28A, (1992), 445-448.
He, Q, et al., "Repair of Flexor Tendon Defects of Rabbit With Tissue Engineering Method", Chinese J. Of Traumatology, 5(4), (2002), 200-208.
Helidonis, E, et al., "Laser Shaping of Composite Cartilage Grafts", Am J Otolaryngology, vol. 14, No. 6, (1993), 410-412.
Hiraki, et al., "Effect of transforming growth factor B on cell proliferation and glycosaminoglycan synthesis by rabbit growth-plate chondrocytes in culture", Biochimica et Biophysica Acta, vol. 969, (1988), 91-99.
Hollander, Anthony P, et al., "Maturation of Tissue Engineered Cartilage Implanted in Injured and Osteoarthritic Human Knees,", Tissue Engineering, vol. 12, No. 7, Mary Ann Leibert, Inc., UK, (2006), 1787-1798.
Hollinger, Jeffrey O, et al., "Poly(alpha-hydroxy acids): carriers for bon morphogenetic proteins", Biomaterial, vol. 17, (1996), 187-194.
Homminga, G N, "Repair of Chondral Lesions of the Knee with e Perichondrial Graft, Fibrin Sealant in Operative Medicine", Orthopedic Surgery Maxillofacial Surgery, vol. 4, Springer-Verlag, Berlin Heidelberg, (1986), 61-69.
Hoover, N W, et al., "Skin Arthroplasty of the Hip, An Experimental Study in Dogs", JBJS, vol. 43-A, No. 8, (1961), 1155-1166.
Horton, et al., "Transforming growth factor-beta and fibroblast growth factor act synergistically to inhibit collagen II synthesis through a mechanism involving regulatory DNA sequences", Journal of Cellular Physiology, vol. 141, (1989), 8-15.
Horton, W., et al., "Characterization of a Type II Collagen Gene (COL2A1) Mutation Identified in a Cultured Chondrocytes from Human Hypochondrogenesis", PNAS, V. 89, (1992), 4583-4587.
Hu, Wei-Shou, "Bioreactors for Animal Cell Cultivation", Recent Advances in Biotechnology, Kluwer Academic Publishers, Netherlands, (1992), 243-261.
Hunter, W, Vi, "Of the Structure and Difeafes of Articulating Cartilages", Academiae Grypeswaldensis Bibliotheca, vol. 1, (1775), 514-521.
Hurtig, M B, et al., "Effects of Lesion Size and Location on Equine Articular Cartilage Repair", Can J Vet Res, vol. 52, (1988), 137-146.
Imhoff, A B, et al., "Autologous Osteochondral Transplantation on Various Joints", English Abstract Only, Orthopade, vol. 28, No. 1, (1999), 33-44.
Ishida, T, "The Use of a Fibrin Adhesive for a Cartilage Graft Basic and Clinical Studies", English Abstract Only, Japanese J of Plastic and Reconstructive Surgery, vol. 33, No. 1, (1990), 215-230.
Ishizaki, Y., et al., "Autocrine Signals Enable Chondrocytes to Survive in Culture", J. Cell. Biol., 126(4), (1994), 1069-1077.
Ito, Y, et al., "Localization of chondrocyte precursors in periosteum", Osteoarthritis and Cartilage, vol. 9, (2001), 251-223.
Ittner, G, et al., "Treatment of Flake Fracture of the Talus", Z Orthop Ihre Grenzgeb, vol. 127, No. 2, English Abstract Only, (1989), 183-6.

Iwasa, J, et al., "Clinical application of scaffolds for cartilage tissue engineering", Surg Sports Traumalol Arthorsc vol. 13, No. 4, (2007), 693-703.
Jakob, et al., "Autologous Osteochondral Grafting in the Knee: Indication, Results and Reflections", Clinical Orthopaedics and Related Research, No. 401, (2002), 170-184.
Jin, C, et al., "Human Amniotic Membrane as a Delivery Matrix for Articular Cartilage Repair", Tissue Engineering, 13(4), (2007), 693-703.
Jones, C W, et al., "Matrix-induced autologous chondrocyte implantation in sheep: objective assessments including confocal arthroscopy", J. Orthopaedic Research vol. 26, (2008), 292-303.
Jurgensen, K, et al., "A New Biological Glue for Cartilage-Cartilage Interfaces: Tissue Transglutaminase", JBJS (Am), 1997, vol. 79., (1997), 185-193.
Kallio, K E, "Arthroplastia Cutanea, Discussion by T. Heirtom", ACTA Orthopaedica Scandinavica, vol. 26, (1957), 327-328.
Kandel, et al., "Fetal bovine serum inhibits chondrocyte collagenase production: interleukin 1 reverses this effect", Biochim. Biophys. Acta.: 1053(2-3), (1990), 130-134.
Kanzaki, J, et al., "Use of Fibrin Glue in Intracranial Procedures Following Acoustic Nouroma Surgery: Application in Facial Nerve Reconstruction and Prevention of Cerebrospinal Fluid Rhinorrhea, Fibrin Sealing in Surgical and Nonsurgical Fields", Neurosurgery Ophthalmic Surgery ENT, vol. 5, Springer-Verlag, Berlin, Heidelberg, (1994), 162-168.
Kato, Y, et al., "Sulfated Proteoglycan Synthesis by Conftuent Cultures of Rabbit Costal Chondrocytes Grown in the Presence of Fibroblast Growth Factor", J. Cell Biology, vol. 100., (1985), 477-485.
Kavalkovich, Karl W, et al., "Chondrogenic Differentiation of Human Mesenchymal Stem Cells Within an Alginate Layer Culture System", In Vitro Cell. Dev. Biol.-Animal, vol. 38, Society for In Vitro Biology, USA, (2002), 457-466.
Keller, J, et al., "Fixation of Osteochondral Fractures", Acta Orthop Scand, vol. 56, (1985), 323-326.
Kettunen, K O, "Skin Arthroplasty in the Light of Animal Experiments With Special Reference to Functional Metalasia of Connective Tissue", Acta Ortho Scand, Suppl XXIX, (1958), 9-69.
Kimura, Tomoatsu, et al., "Chondrocytes Embedded in CoHagen Gels Maintain Cartilage Phenotype During Long-term Cultures", ?Clinical Orthopaedics and related Research, vol. 186, Japan, (1984), 231-239.
Klagsbrun, et al., "Purification of a cartilage-derived growth factor", The Journal of Biological Chemistry, vol. 255, No. 22, (1980), 10859-10866.
Klagsbrun, et al., "The stimulation of DNA synthesis and cell division in chondrocytes and 3T3 cells by a growth factor isolated from cartilage", Exp Cell Res, vol. 105, (1977), 99-108.
Klein, T J, et al., "Tailoring secretion of proteoglycan 4 (PRG4) in tissue-engineered cartilage", Tissue Engineering, vol. 12, No. 6., (2006), 1429-1439.
Klein, T J, et al., "Tissue engineering of stratified articular cartilage from chondrocyte subpopulations", OsteoArthritis and Cartilage vol. 11, (2003), 595-602.
Kon, E, et al., "Arthroscopic second generation autologous chondrocyte implantation at 48 months follow up", Osteoarthritis and Cartilage vol. 15, Suppl. B, (2007), B44-45.
Kon, E, et al., "Arthroscopic Second-generation Autologous Chondrocyte Implantation Compared with Microfracture of Chondral Lesions of the Knee", Am J. Of Sports Medicine vol. 37, No. 1, (2009), 33-41.
Kon, E, et al., "Second Generation Issues in Cartilage Repair", Sports Med Arthorosc Rev., 16(4), (2008), 221-229.
Korhonen, R K, et al., "Importance of the superficial tissue layer for the indentation stiffness of articular cartilage", Medical Eng Phys, vol. 24, (2002), 99-108.
Krueger, John W, et al., "An In Vitro Study of Flow Response by Cells", Journal of Biomechanics, vol. 4, Pergamon Press, Great Britain, (1971), 31-36.
Kuettner, Klaus E, et al., "Synthesis of Cartilage Matrix by Mammalizn Chondrocytes In Vitro.I. Isolation, Culture Characteristics, and Morphology", the Journal of Cell Biology, vol. 93, The RockefeHer University Press, USA, (1982), 743-750.

Kujawa, et al., "Hyaluronic acid bonded to cell culture surfaces inhibits the program of myogenesis", Developmental Biology, vol. 113, (1986), 10-16.

Kujawa, Mary J, et al., "Hyaluronic Acid Bonded to Cell-Culture Surfaces Timulates Chondrogenesis inStage 24 Limb Mesenchyme Cell Cultures", Developmental Biology, vol. 114, Academic Press, Inc., USA, (1986), 504-518.

Kujawa, Mary J, et al., "Substrate-Bonded Hyaluronic Acid Exhibits a Size-Dependent Stimulation of Chondrogenic Differentiation of Stage 24 Limb Mesenchymal Cells in Culture", Developmental Biology, vol. 114, Academic Press, Inc., USA, (1986), 519-528.

Lane, J. M, et al., "Joint Resurfacing in the Rabbit Using an Autologous Osteochondral Graft", JBJS, vol. 59-A, No. 2, (1977), 218-222.

Langer, F, et al., "Immunogenicity of Allograft Articular Cartilage", JBJS, vol. 56-A, No. 2, (1974), 297-304.

Langer, F, et al., "The Immunogenicity of Fresh and Frozen Allogenic Bone", JBJS, vol. 57-A, No. 2, (1975), 216-220.

Lavrishcheva, G I, "Filling Bone Cavities with Minced Cartilage", Ortopediia Travmatologiia I Protezirovanie, vol. 1, (1955), 80.

Lee, et al., "Primary cultured chondrocytes of different origins respond differently to bFGF and TGF-B", Life Sciences, vol. 61, No. 3, (1997), 293-299.

Lee, J W, "Preplanned Correction of Enophthalmos Using Diced Cartilage Grafts", British J Plastic Surgery, vol. 53, (2000), 17-23.

Lemperg, R, et al., "Transplantation of Diced Rib Cartilage to the Hip Joint. Experimental Study on Adult Dogs", Acta Soc Med Ups, vol. 70, No. 3, (1965), 197-212.

Lennert, K H, et al., "Fibrin Adhesive in the Surgical Treatment of the Pseudoarthrosis of the Scaphoid Bone-Methods and Results", Unfallchirurgie, vol. 14, No. 3, (1988), 158-160.

Libera, J, et al., "Cartilage Engineering, Fundamentals of Tissue Engineering and Regenerative Medicine", Chapter 18, SPringer-Verlag, Berlin Heidelberg, (2009), 233-242.

Limberg, A A, "Supporting and Contour Plastic Repair by Needle Administration of Minced Cartilage", Vestnik Khirurgii Imeni I.I. Grekova, vol. 78, No. 4, (1957), 68-73.

Limberg, A A, "The Use of Diced Cartilage by Injection with a Needle. Part 1. Clinical Investigations", Plast Reconstr Surg Transient Bull, vol. 28, (1961), 523-36.

Limberg, A A, "The Use of Diced Cartilage by Injection with a Needle. Part 2. Morphologic Changes in the Diced Human Cartilage After Auto- and Homoplasty", Plast Reconstr Surg Transplant Bull, vol. 28, (1961), 649-655.

Lin, Z, et al., "Gene Expression Profiles of Human Chondrocytes during Passaged Monolayer Cultivation", J. Orthopaedic Research, vol. 26, (2008), 1230-1237.

Liu, Lin-Shu, et al., "An osteoconductive collagen/hyaluronate matrix for bone regeneration", Biomaterials vol. 20, Elsevier, UK, (1999), 1097-1108.

Liu, X, et al., "In vivo ectopic chondrogenesis of BMSCs directed by mature chondrocytes", Biomaterials, vol. 31, (2010), 9406-9414.

Loeb, L, "Autotransplantation and Homoiotransplantation of Cartilage in the Guinea-pig", Am. J. Pathology, V. II, (1926), 111-122.

Lucas, Paul A, et al., "Ectopic induction of cartilage and bone by water-soluble proteins from bovine bone using a collagenous delivery vehicle", Journal of Biomedical Materials Research: Applied Biomaterials, vol. 23, No. Al, (1989), 23-39.

Lucht, U, et al., "Fibrin Sealant in Bone Transplantation. No Effects on Blood Flow and Bone Formation in Dogs", Acta Orthop Scand, vol. 57, No. 1, (1986), 19-24.

Luyten, Frank P, et al., "Articular Cartilage Repair: Potential Role of Growth and Differentiation Factors", Biological Regulation ofthe Chondrocytes, USA, 227-236.

Mackay, et al., "Chondrogenic differentiation of cultured human mesenchymal stem cells from marrow", Tissue Engineering, vol. 4, No. 4, (1998), 415-430.

Malemud, C J, et al., "The effect of chondrocyte growth factor on membrane transport by articular chondrocytes in monolayer culture", Connective Tissue Research, vol. 6, (1978), 1-9.

Maletius, W, et al., "Refixation of Large Chondral Fragments on the Weight-Bearing area of the Knee Joint: A Report of Two Cases", Arthroscopy, vol. 10, No. 6, (1994), 630-33.

Mandl, E W, et al., "Multiplication of human chondrocytes with low seeding densities accelerates cell yield without losing redifferentiation capacity", Tissue Engineering, vol. 10, No. 1/2, (2004), 109-120.

Mandl, E W, et al., "Serum-free medium supplemented with high-concentration FGF2 for cell expansion culture of human ear chondrocytes promotes redifferentiation capacity", Tissue Engineering, vol. 8, No. 4, (2002), 573-582.

Mankin, H J, "Current Concepts Review, The Response of Articular Cartilage to Mechanical Injury", JBJS, vol. 64, No. 3, (1982), 460-6.

Mankin, H J, "Localization of Tritiated Thymidine in Articular Cartilage of Rabbits: II. Repair in Immature Cartilage", JBJS, V. 44, (1962), 688-698.

Mankin, H J, "Localization of Tritiated Thymidine in Articular Cartilage of Rabbits: III. Mature Articular Cartilage", JBJS, V. 45, (1963), 529-540.

Mannhelm, A, "Free Autoplastic Cartilage Transplantation", Abstract, J Am Med Assoc, vol. 87, No. 25, (1926), 2132.

Marcacci, M, et al., "Multiple Osteochondral Arthroscopic Grafting (Mosaicplasty) for Cartilage Defects of the Knee: Prospective Study Results at 2-Year Follow-up", J. Arthroscopic & Related Surgery, vol. 21, No. 4., (2005), 462-470.

Marcacci, M, et al., "Use of Autologous Grafts for Reconstruction of Osteochondral Defects of the Knee", Orthopedics, vol. 22, No. 6, (1999), 959-600.

Marchac, D, et al., "Face Lifts and Sprayed Fibrin Glue: An Outcome Analysis of 200 patients", Br J Plast Surg, vol. 47, No. 5, (1994), 306-09.

Marchac, D, et al., "Fibrin Glue Fixation in Forehead Endoscopy: Evaluation of our Experience with 206 Cases", Plast Reconstr Surg, vol. 100, No. 3, (1997), 713-14.

Marlovits, S, et al., "Changes in the ratio of type-I and type-II collagen expression during monolayer culture of human chondrocytes", JBJS, vol. 86-B, (2004), 286-95.

Marlovits, Stefan, et al., "Early postoperative adherence of matrix-induced autologous chondrocyte implantation for the treatment of full-thickness cartilage defects of the femoral condyle", Knee Surg Sports Traumatol Arthorosc, vol. 13, Springer-Verlag, Austria, (2005), 451-457.

Mathiowitz, Edith, et al., "Biologically erodable microspheres as potential oral drug delivery systems", Nature, vol. 386, (Mar. 1997), 410-414.

Matras, H, "Fibrin Seal: The State of the Art", J Oral Maxilofac Surg, vol. 43, (1985), 605-611.

Matsusue, Y, et al., "Biodegradable Pin Fixation of Osteochondral Fragments of the Knee", Clin Ortho Rel Res, No. 322, (1996), 166-173.

McKibbin, B, "Immature Joint Cartilage and the Homograft Reaction", JBJS, V. 53-B, No. 1, (1971), 123-135.

McNickle, Allison G, et al., "Overview of Existing Cartilage Repair Technology", Sports Med Arthorosc Rev., vol. 16, No. 4, Lippincott Williams & Wilkins, USA, (2008), 196-201.

McQueen, Anne, et al., "Flow Effects on the Viability and Lysis of Suspended Mammalian Cells", Biotechnology Letters, vol. 9, No. 12, California Institute of Technology, USA, (1987), 831-836.

Merchuk, Jose Celman, "Shear Effects on Suspended Cells", Advances in Biochemical Engineering Biotechnology, vol. 44, Springer-Verlag Berlin Heidelberg, (1988).

Merchuk, Jose C, et al., "Why use air-lift bioreactors?", Tibtech, vol. 8, Elsevier Science Publishers Ltd., UK, (1990), 66-71.

Meyers, M H, et al., "A Fibrin Adhesive Seal for the Repair of Osteochondral Fracture Fragments", Clin Ortho Rel Res, No. 182, (1984), 258-263.

Mienaltowski, M J, et al., "Differential gene expression associated with postnatal equine articular cartilage maturation", BMC Musculoskeletal Disorders, vol. 9., (2008), 149-162.

Minas, T, et al., "Current Concepts in the Treatment of Articular Cartilage Defects", Orthopedics, vol. 20., (1997), 525-538.

Mithofer, K, et al., "Functional Outcome of Knee Articular Cartilage Repair in Adolescent Athletes", Am J Sports Med, vol. 33, No. 8, (2005), 1147-53.

Miura, Y, et al., "Brief Exposure to High-Dose Transforming Growth Factor-Beta 1 Enhances Periosteal Chondrogenesis in Vitro: a Premilinary Report", JBJS, vol. 84-A, No. 5, (2002), 793-9.

Mow, V C, et al., "Experimental Studies on Repair of Large Osteochondral Defects at a High Weight Bearing Area of the Knee Joint: A Tissue Engineering Study", Transactions of the ASME, Journal of Biomechanical Engineering, vol. 113, USA, (1991), 198-207.

Murray, M M, et al., "The Migration of Cells From the Ruptured Human Anterior Cruciate Ligament Into Collagen-Glycosaminoglycan Regeneration Templates in Vitro", Biomaterials, vol. 22, (2001), 2393-2402.

Nageotte, J, "The Organization of Matter in its Connections with Life. Studies of General Anatomy and Experimental Morphology on the Connective Tissue and the Nerve", L'Organisation De La Matiere, (1922), 95-98.

Niekisch, V R, "Possible Methods of Using Fibrin-Glue Protection in Maxillo Facial Surgery", English Summary Only. Zahn Mund Kieferheilkd Zentralbl, vol. 68, No. 6, (1980), 555-61.

Nixon, Alan J, et al., "Temporal matrix synthesis and histologic features of a chondrocyte-laden porous collagen cartilage analogue", American Journal of Veterinary Research, vol. 54, No. 2, USA, (1993), 349-356.

Obradovic, B, et al., "Integration of Engineered Cartilage", Journal of Orthop Res, vol. 19, No. 6, (2001), 1089-97.

O'Driscoll, S W, et al., "The Chondrogenic Potential of Free Autogenous Periosteal Grafts for Biological Resurfacing of Major Full-Thickness Defects in Joint Surfaces Under the Influence of Continuous Passive Motion. An Experimental Investigation in the Rabbit.", J Bone Joint Surg Am, vol. 68, No. 7, (1986), 1017-35.

Oegema, T R, et al., "Characterization of a hyaluronic acid-dermatan sulfate proteoglycan complex from dedifferentiated human chondrocyte cultures", J Biol Chem, vol. 256, No. 2, (1981), 1015-1022.

Ohlsen, L, et al., "The Early Development of Articular Cartilage After Perichondral Grafting", Scand J Plast Reconstr Surg, vol. 17, (1983), 163-177.

Oldshue, J Y, et al., "Comparison of Mass Transfer Characteristics of Radial and Axial Flow Impellers", Mixing Proceedings of the 6th European Conference, Pavia, Italy, (1988), 345-350.

Outerbridge, H K, et al., "The Use of a Lateral Patellar Autologous Graft for the Repair of a Large Osteochondral Defect in the Knee", J Bone Joint Surg Am, vol. 77, No. 1, (1995), 65-72.

Paar, O, et al., "Cartilage Adhesion at the Knee Joint, Clinical Follow Up Examination", Akt. Traumatol, vol. 14, (1984), 15-19.

Papoutsakis, Eleftherios T, "Fluid-mechanical damage of animal cells in bioreactors", TibTech, vol. 9, Elsevier Science Publishers Ltd. (UK), (1991), 427-437.

Park, J J, et al., "Comparison of the Bonding Power of Various Autologous Fibrin Tissue Adhesives", Am J Otology, vol. 18, No. 5, (1997), 655-659.

Park, M S, "Tympanoplasty Using Autologous Crushed Cartilage", Rev Laryngol Otol Rhino!, vol. 116, No. 5, (1995), 365-368.

Pascone, M, et al., "Fibrin Sealant in Plastic Surgery of the Head, Plastic Surgery Nerve Repair Burns, Fibring Sealing in Surgical and Nonsurgical Fields", vol. 3, Springer-Verlag, Berlin Heidelberg, (1995), 11-15.

Passl, et al., "Morphological and Therapeutic Aspects of Osteochondrosis dissecans and Aseptic Bone Necroses", Acta Medica Austriaca, Suppl No. 11, (1978), 17-18.

Passl, R, et al., "Fibrin Gluing of Cartilage Surfaces-Experimental Studies and Clinical Results", Med U Sport, vol. 19 (1/2), (1979), 23-28.

Passl, R, et al., "Histological Observations After Replantation of Articular Cartilage Using Fibrin Sealant", Traumatology and Orthopaedics vol. 7, (1986), 190-198.

Passl, R, et al., "Homologous Articular Cartilage Transplantation in Animal Experiments. Preliminary Studies on Sheep (authors transl)", Arch Orthop Unfallchir, vol. 86, No. 2, (1976), 243-56.

Passl, R, et al., "Homologous Cartilage Transplants in Animal Experiments", 4th Orthopedics Symposium, Heidelberg, Horst Cotta and Arnim Braun (eds), Georg Thieme Verlag Stuttgart, New York, (1981), 102-105.

Passl, R, et al., "Problems of Pure Homologous Articular Cartilage Transplantation", Verh Anat Ges, vol. 70, (1976), 675-678.

Pavesio, Allesandra, et al., "Hyaluronan-based scaffolds (Hyalograft C) in the treatment of knee cartilage defects; preliminary clinical findings", Hyaluronan Scaffolds in Cartilage Repair, UK, (2003), 203-217.

Pech, A, et al., "Tissuecol in Septorhinoplasties", Ann Oto-Laryng, vol. 105, Abstract Only, (1988), 629-634.

Peer, L A, "Extended Use of Diced Cartilage Grafts", Meeting of the American Association of Plastic Surgeons, (Apr. 21, 23, 1954), 178-185.

Peer, L A, "Fate of Autogenous Septal Cartilage After Transplantation in Human Tissues", Archive of Otolaryngology, vol. 34, No. 4, (1941), 696-709.

Peer, L A, "The Fate of Living and Dead Cartilage Transplanted in Humans", Surg Gynec, and Obst, vol. 68, (1939), 603-610.

Peer, L A, "The Neglected Septal Cartilage Graft (With Experimental Observations on the Growth of Human Cartilage Grafts)", Arch Otolaryngol Head Neck Surg, vol. 42, No. 5, (1945), 384-396.

Peer, L. A, "Transplantation of Tissues-Cartilage, Bone, Fascia, Tendon, and Muscle",The Williams & Wilkins Company, vol. 1, Baltimore, Maryland USA, vol. 1, (1955), 69-137 & 392-393.

Peretti, G M, et al., "Meniscal repair using engineered tissue", J. Orthop Res, vol. 19, No. 2., (2001), 278-85.

Phemister, D B, et al., "The Method of New Joint Formation in Arthroplasty, Surgery, Gynecology and Ostetrics", vol. 26, (1918), 406-447.

Pierce, G W, et al., "Reconstruction Surgery of the Nose", XXXVI, Ann Otol Rhin and Laryng, vol. 47, (1938), 437-452.

Pieter, A, et al., "Effect of Purified Growth Factors on Rabbit Articular Chondrocytes in Monolayer Culture, I", DNA Synthesis, Arthritis & Rheumatism, vol. 25, No. 10, (1982), 1217-1227.

Piragine, F, et al., "Use of Bovine Heterologous Cartilage and Fibrin Sealant in Middle Ear Reconstructive Surgery", Neurosurgery Ophthalmic Surgery Ent, Fibrin Sealing in Surgical and Nonsurgical Fields, vol. 5, Springer-Verlag, New York USA, (1994), 193-198.

Pirsig, W, et al., "Regeneration of Septal Cartilage in Children after Septoplasty. A histological Study.", English Abstract only. Acta Otolaryngol, vol. 79, No. 5-6, (1975), 451-9.

Pitman, M I, et al., "The Use of Adhesives in Chondrocyte Transplantation Surgery: In-Vivo Studies", Bull Hosp Jt Dis Orthop Inst, vol. 49, No. 2, (1989), 213-20.

Plaga, B R, et al., "Fixation of Osteochondral Fractures in Rabbitt Knees. A Comparison of Kirschner Wires, Fibrin Sealant, and Polydioxanone Pins", Journal Bone Joint Surg Br, vol. 74, No. 2, (1992), 292-6.

Plenk, H Jr, et al., "Trans- and Replantation of Articular Cartilage Using the Fibronogen Adhesive System", Gastpar, H (ed). Biology of the articular Cartilage in Health and Disease, Schattauer, Stuttgart, New York, USA, (1980), 439-447.

Redl, H, et al., "Methods of Fibrin Seal Application", Thorac Cardiovasc Surgeon, vol. 30, (1982), 223-227.

Reginato, et al., "Formation of nodular structures resembling mature articular cartilage in long-term primary cultures of human fetal epiphyseal chondrocytes on a hydrogel substrate", Arthritis & Rheumatism, vol. 37, No. 9, (1994), 1338-1349.

Roberts, S, et al., "Autologous Chondrocyte Implantation for Cartilage Repair: Monitoring its Success by Magnetic Resonance Imaging and Histology", Arthritis Res and Therapy, vol. 5, (2003), R60-R73.

Rohrbach, J M, et al., "Biological Corneal Replacement an Alternative to Keratoplasty and Keratoprosthesis? A Pilot Study With Heterologous Hyaline Cartilage in the Rabbit Model", Abstract Only, Klin Monatsbl Augenheikd, vol. 207, No. 3, (1995), 191-6.

Ronga, Mario, et al., "Arthroscopic Autologous Chondrocyte Implantation for the Treatment of a Chondral Defect in the Tibial Plateau of the Knee", Arthroscopy: the Journal of Arthroscopic and Related Surgery, vol. 20, No. 1, Italy, (2004), 79-84.

Ronga, Mario, et al., "Tissue Engineering Techniques for the Treatment of a Comples Knee Injury", Arthroscopy: The Journal of Arthroscopic and Related Surgery, vol. 22 No. 5, Italy, (2006), 576. e1-576.e3.

Rosier, R N, et al., "Transforming growth factor bela: an autocrine regulator of chondrocytes", Connective Tissue Research vol. 20., (1989), 295-301.

Rosselot, G, et al., "Development of a serum-free system to study the effect of growth hormone and insulinlike growth factor-I on cultured postembryonic growth plate chondrocytes", In Vitro Cell Dev Biol vol. 28A., (1992), 235-244.

Ruano-Ravina, A, et al., "Autologous Chondrocyte Implantation: A Systematic Review", Osteoarthritis and Cartilage, vol. 14, (2006), 47-51.

Rudderman, R H, et al., "The Fate of Fresh and Preserved, Noncrushed and Crushed Autogenous Cartilage in the Rabbit Model", Ann Plastic Surgery, vol. 32, (1994), 250-254.

Rupp, G, et al., "Fibrin Adhesion of Transposed Autologous Cartilage Bone Grafts to Repair Knee-Joint Defects", Langenbeck's Archives of Surgery, vol. 347, No. 1, (1978), 676-677.

Russlies, M., et al., "A cell-seeded biocomposite for cartilage repair", Annals of Anatomy vol. 184, Urban & Fischer Verlag, UK, (2002), 317-323.

Saidi, K, et al., "Articular Knee Transplant in the Rabbit: Experimental Study and Clinical Projections", Union Medicale du Canada, vol. 100, No. 1, (1971), 88-99.

Saini, Sunil, et al., "Concentric Cylinder Bioreactor for Production of Tissue Engineered Cartilage; Effect of Seeding Density and Hydrodynamic Loading on Construct Development", Biotechnol Prog., vol. 19, American Chemical Society and American Institute of Chemical Engineers, USA, (2003), 510-521.

Salter, R B, et al., "The Biological Effect of Continuous Passive Motion on the Healing of Full-Thickness Defects in Articular Cartilage", JBJS, vol. 62-A, No. 8, (1980), 1232-1251.

Salter, Robert B, et al., "The Biological Concept of Continuous Passive Motion of Synovial Joints: The First 18 Years of Basic Research and Its Clinical Application", Articular Cartilage and Knee Joint Function : Basic Science and Arthroscopy, Raven Press, Ltd., NY, USA, (1990), 335-353.

Sampath, T K, et al., "In Vitro Transformation of Mesenchymal Cells Derived from Embryonic Muscle into Cartilage in Response to Extracellular Matrix components of bone", Proc Natl Acad Sci USA, vol. 81, No. 11, (1984), 3419-23.

Schlag, G, et al., "Fibrin Adhesive System in Bone Healing", Acta Orthop Scand, vol. 54, No. 4, (1983), 655-8.

Schlag, G, et al., "Fibrin Sealant in Orthopedic Surgery", Clin Ortho Rel Res, vol. 227, (1988), 269-285.

Schmidt, Tannin A, et al., "Synthesis of Proteoglycan 4 by Chondrocyte Subpopulations in Cartilage Explants, Monolayer Cultures, and Resurfaced Cartilage Cultures", Arthritis & Rheumatism, vol. 50, No. 9, American College of Rheumatology, USA, (2004), 2849-2857.

Schobel, H, et al., "Compound Prosthesis and Cartilage Layer: Two New Applications of Fibrin Sealing in Reconstructive Middle Ear Surgery, Neurosurgery Ophthalmic Surgery ENT", Fibrin Sealing in Surgical and Nonsurgical Fields, vol. 5, Springer-Verlag, New York, USA, (1994), 186-192.

Schreiber, R E, et al., "A Method for Tissue Engineering of Cartilage by Cell Seeding on Bioresorbable Scaffolds", Ann NY Acad Science, vol. 875, (1999), 398-404.

Schubert, T, et al., "Long-term effects of chondrospheres on cartilage lesions in an autologous chondrocyte implantation model as investigated in the SCID mouse model", International Journal of Molecular Medicine, vol. 23, (2009), 455-460.

Schwan, B L, "Human Amniotic Membrane Transplantation for the Treatment of Ocular Surface Disease", Human Amniotic Membrane Transplantation, (2002), 1-7.

Schwarz, E R, et al., "Sulfate Metabolism in Human Chondrocyte Cultures", J Clin Investigation, vol. 54, (1974), 1056-1063.

Schwarz, N, et al., "The Influence of Fibrin Sealant on Demineralized Bone Matrix-Dependent Osteoinduction", Clin Ortho Rel Re, No. 238, (1989), 282-287.

Schwarz, Ray P, et al., "Cell Culture for Three-Dimensional Modeling in Rotating-Wall Vessels: An Application of Simulated Microgravity", Journal of Tissue Culture Meth., Tissue Culture Association, TX, USA, (1992), 51-58.

Shahgaldi, B F, et al., "Repair of Cartilage Lesions Using Biological Implants—A Comparative Histological and Biomechanical Study in Goats", Journal of Bone & Joint Surgery, vol. 73-5, UK, (1991), 57-64.

Shoemaker, S, et al., "Effects of Fibrin Sealant on Incorporation of Autograft and Xenograft Tendons Within Bone Tunnels. A Preliminary Study.", American Journal of Sports Medicine, vol. 17, No. 3, (1989), 318-24.

Simms, G F, et al., "Diced Homologous Cartilage in Hemioplasty", Jour Med Soc J J, vol. 49, No. 9, (1952), 406-7.

Smith, R. Lane, et al., "Effects of Fluid-Induced Shear on Articular Chondrocyte Morphology and Metabolism In Vitro", Journal of Orthopaedic Research, The Journal of Bone and Joint Surgery, Inc., vol. 13, USA, (1995), 824-831.

Sokoloff, L, et al., "In vitro culture of articular chondrocytes", Federation Proc vol. 32., (1973), 1499-1502.

Sokoloff, L., et al., "Sulfate Incorporation by Articular Chondrocytes in Monolayer Culture", Arthritis and Rheumatism vol. 13, No. 2., (1970), 118-124.

Song, C. X, et al., "Formulation and Characterization of Biodegradable Nanoparticles for Intravascular Local Drug Delivery", Journal of Controlled Release vol. 43, No. 2/03, XP00632668, (Jan. 18, 1997), 197-212.

Sosna, A, et al., "Use of Fibrin Glue in Orthopedics", Acta Chir Orthop Traum, vol. 51, No. 2, (1984), 8-91.

Spangenberg, K M, et al., "Histomorphometric Analysis of a Cell-Based Model of Cartilage Repair", Tissue Engineering, vol. 8, No. 5., (2002), 839-46.

Stathopoulos, N. A, et al., "Shear Stress Effects on Human Embryonic Kidney Cells in Vitro", Biotechnology and Bioengineering, vol. XXVII, John Wiley & Sons, Inc., USA, (1985), 1021-1026.

Stewart, Matthew C, et al., "Phenotypic Stability of Articular Chondrocytes In Vitro: The Effects of Culture Models, Bone Morphogenetic Protein 2, and Serum Supplemenation", Journal of Bone and Mineral Research, vol. 15, No. 1, (2000), 166-174.

Stiles, C. D, et al., "Dual control of cell growth by somatomedins and platelet-derived growth factor", PNAS vol. 76, No. 3., (1979), 1279-1283.

Stockwell, R. A, "The cell density of human articular and costal cartilage", J. Anal. vol. 101,No. 4., (1967), 753-763.

Tanaka, H, et al., "A Study on Experimental Homocartilage Transplantation", Arch Orthop Traumat Surg, vol. 96, (1980), 165-169.

Tanaka, H, et al., "Histochemical Studies on Regeneration of Articular Cartilage", Tokushima J Exp Med, vol. 18, (1971), 63-73.

Thilly, W. G, et al., "Microcarrier Culture: A Homogeneous Environment for Studies of Cellular Biochemistry", Methods in Enzymology vol. LVIII, ISBN 0-12-181958-2, Academic Press, Inc., New York, New York, United States., (1979), 184-194.

Thilly, W. G, et al., "Microcarriers and the problem of high density cell culture", From Gene to Protein: Translation in Biotechnology vol. 19, Academic Press, Inc., New York, New York, United States., (1982), 75-103.

Trattnig, S., et al., "Differentiating normal hyaline cartilage from post-surgical repair tissue using fast gradient echo imaging in delayed gadolinium-enhanced MRI (dGEMRIC) at 3 Tesla", Eur Radial vol. 18., (2008), 1251-1259.

Trattnig, S., et al., "Quantitative T2 Mapping of Matrix-Associated Autologous Chondrocyte Transplantation at 3 Tesla an in vivo Cross-Sectional Study", Investigative Radiology vol. 42, No. 6., (2007), 442-448.

Trattnig, Siegfried, et al., "Matrix-based autologous chondrocyte implantation for cartilage repair: noninvasive monitoring by high-resolution magnetic resonance imaging", Magnetic Resonance Imaging, vol. 23, Elsevier, Austria, (2005), 779-787.

Tuan, R, "A Second-Generation Autologous Chondrocyte Implantation Approach to the Treatment of Focal Articular Cartilage Defects", Arthritis Research & Therapy, V. 9, (2007), 109-112.

Vacant!, C. A, et al., "Synthetic Polymers Seeded with Chondrocytes Provide a Template for New Cartilage Formation", Plastic and Reconstructive Surgery, vol. 88, No. 5, (1991), 753-759.

Vachon, A, et al., "Neochondrogenesis in free Intra-Articular, Periosteal, and Perichondrial Autografts in Horses", American Journal Vet Res, vol. 50, No. 10, (1989), 1787-1794.

Vanderploeg, E. J, et al., "Articular chondrocytes derived from distinct tissue zones differentially respond to in vitro oscillatory tensile loading", Osteoarthritis and Cartilage vol. 16., (2008), 1228-1236.

Venkat, Raghavan V, et al., "Study of Hydrodynamics in Microcarrier Culture Spinner Vessels: A Particle Tracking Velocimetry Approach", Biotechnology and Bioengineering, vol. 49, John Wiley & Sons, Inc., USA, (1996), 456-466.

Verwerd, C.D.A., et al., "Wound Healing of Autologous Implants in the Nasal Septal Cartilage", ORL, vol. 53, (1991), 310-314.

Vishwakarma, G. K, et al., "Isolation & cryo-preservation of human foetal articular chondrocytes", Indian J. Med Res vol. 98., (1993), 309-313.

Von Schroeder, Herbert P, et al., "The use of polylatic acid matrix and periosteal grafts for the reconstruction of rabbit knee articular defects", Journal of Biomedical Materials Research, vol. 25, (1991), 329-339.

Wagner, P D, et al., "Improved Blood Buffering in High-Altitude Natives?", J Appl Physiol, vol. 93, (2002), 2214-2215.

Wei, X, et al., "The Effect of Sodium Selenite on Chondrocytes in Monolayer Culture", Arthritis and Rheumatism, vol. 29, No. 5, (1986), 660-664.

Welsh, F, et al., "The Alar Cartilage Morseler: A New Instrument", Br J Plastic Surgery, vol. 36, (1983), 483-484.

Wilflingseder, P, "Cranioplasties by Means of Diced Cartilage and Split Rib Grafts", Min Chir, vol. 38, No. 12, (1983), 837-43.

Willers, Craig, et al., "Articular cartilage repair: procedures versus products", Expert Rev. Med. Devices, vol. 4., No. 3, Future Drugs Ltd, US, (2007), 373-392.

Wischhofer, E, et al., "The Behaviour of Autologous Spongiosa Transplants from the Dial Crest With and Without Fibrinadhesive in the Canine Femoral Epiphysis", English abstarct only. Unfallheilkunde, vol. 85, (1982), 250-252.

Xu, et al., "Injectable Tissue-Engineered Cartilage with Different Chondrocyte Sources", vol. 113, (2004), 1361-1371.

Yoshihashi, Yuji, et al., "Tissue Reconstitution by Isolated Articular Chondrocytes in vitro", J. Jpn. Orthop. Assoc., vol. 58, (1983), pp. 629-641.

Young, F, "Autogenous Cartilage Grafts, An Experimental Study", Surgery, vol. 10, (1941), 7-20.

Young, F, "The Use of Autogenous Rib Cartilage Grafts to Repair Surface Defects in Dog Joints", Surgery, vol. 7, (1940), 254-263.

Zahn, F, "On the Fate of Tissues Implanted in the Organism", Int Med Congr in Geneva, Biology Secion, (Sep. 11, 1877), 1-4.

Zalzal, G., "Cartilage Grafts—Present Status", Head & Neck Surgery, (1986), 363-374.

Zheng, M H, et al., "Matrix-induced autologous chondrocyte implantation (MACI): Biological and Histological Assessment", Tissue Engineering, vol. 13, No. 4., (2007), 737-746.

Zilch, H, et al., "Fibrin glue in osteochondral fractures with small fragments of the upper limb", English summary only. Ann. Chir. Main, vol. 6 No. 2, (1987), 173-176.

Zilch, H, et al., "Fixation of Small Osteochondral Fragments with the Fibrinogel Adhesive", English summary only. Clinical Report, Ann Chir Main, vol. 12, (1980), 77-81.

Zilch, H, et al., "Fixing of Osteochondral Fragments with Fibrinogen Glue. Clinical Experiences.", Akt. Taumatol, vol. 11, (1981), 136.

Zilch, V H, "Animal Experiments Investigating the Fixation of Small Osteochondral Fragments by Means of Fibrin Glue", Handchirurgie, vol. 12, (1980), 71-5.

Zilch, V H, et al., "Gluing Small Osteochondral Fragments with Fibrin Glue in Hand Surgery. Clinical Experiences.", Handchirurgie, vol. 12, (1980), 77-81.

Zimber, M P, et al., "TGF-β Promotes the Growth of Bovine Chondrocytes in Monolayer Culture and the Formation of Cartilage Tissue on Three-Dimensional Scaffolds", Tissue Engineering, vol. 1, No. 3., (1995), 289-300.

U.S. Appl. No. 13/327,265, filed Dec. 15, 2001, Apparatus for Forming an Implant.

U.S. Appl. No. 11/613,319, filed Dec. 20, 2006, Apparatus for Delivering a Biocompatible Material to a Surgical Site and Method of Using Same.

U.S. Appl. No. 60/528,865, filed Dec. 11, 2003, Particulate Cartilage System.

U.S. Appl. No. 12/861,404, filed Aug. 23, 2010, Particulate Cartilage System.

U.S. Appl. No. 12/976,689, filed Dec. 22, 2010, Treatment Methods Using a Particulate Cartilage System.

U.S. Appl. No. 12/976,704, filed Dec. 22, 2010, Particulate Cartilage System.

U.S. Appl. No. 12/976,711, filed Dec. 22, 2010, Particulate Cartilage Treatment Composition.

U.S. Appl. No. 12/751,230, filed Mar. 31, 2010, Apparatus and Method for Delivering a Biocompatible Material to a Surgical Site.

U.S. Appl. No. 13/327,238, filed Dec. 15, 2011, Cartilage Implant.

U.S. Appl. No. 13/327,286, filed Dec. 15, 2011, Method of Treating an Ostechondral Defect.

U.S. Appl. No. 12/063,291, filed Dec. 10, 2008, Implants and Methods For Repair, Replacement and Treatment of Disease.

U.S. Appl. No. 12/101,553, filed Apr. 11, 2008, Compositions and Methods for Tissue Repair.

* cited by examiner

METHOD OF OBTAINING VIABLE SMALL TISSUE PARTICLES AND USE FOR TISSUE REPAIR

CROSS REFERENCE TO RELATED APPLICATION

This application is a continuation of and claims the benefit of priority under 35 U.S.C. §120 to Yao et al., U.S. patent application Ser. No. 11/613,250, titled "METHOD OF OBTAINING VIABLE SMALL TISSUE PARTICLES AND USE FOR TISSUE REPAIR," filed on Dec. 20, 2006, which is incorporated herein by reference in its entirety.

TECHNICAL FIELD OF THE INVENTION

Preparation and use of tissue particles, sized from various sources, to repair tissue defects such as orthopedic tissue defects.

BACKGROUND

Articular cartilage is a thin, smooth, low friction, gliding surface composed of hyaline cartilage with resiliency to compressive forces. While only a few millimeters thick, it has excellent wear characteristics. Its mechanical and structural capacity depends on the integrity of its extracellular matrix, in which chondrocytes are sparsely distributed throughout structural macromolecules including collagen, proteoglycans, and noncollagenous proteins. Although chondrocyte cells produce the extracellular matrix, they compose less than 5% of the wet weight of cartilage.

The composition and highly complicated interaction of these components make regeneration and replacement techniques challenging. For example, the lack of a direct blood supply and few cells distributed widely among a dense extracellular matrix leads to a limited healing ability of damaged articular cartilage. This has led to a wide variety of treatment approaches for defects, for example, in the knee, with varying levels of success.

Procedures such as drilling, abrasion, microfracture, and debridement provide symptomatic pain relief and improved function. Collectively, these procedures may be referred to as subchondral bone marrow stimulation techniques where the bone underlying the cartilage, which has a rich blood supply, is caused to bleed. The goal of such procedures is to mobilize mesenchymal stem cells from the blood to differentiate into chondrocyte-like cells that synthesize repair tissue. Once the vascularized cancellous bone is disrupted, a fibrin clot forms and pluripotent cells migrate into the area. These cells eventually differentiate into chondrocyte-like cells that secrete type I, type II and other collagen types, as well as cartilage specific proteoglycans, after receiving appropriate mechanical and biological cues. The cells produce a fibroblastic repair tissue that on appearance and initial biopsy can have a hyaline-like quality, but over time, is demonstrated histologically as being predominantly fibrocartilaginous tissue. Fibrocartilage is a relatively disorganized lattice of collagen fibers, as opposed to the natural hyaline cartilage, and thus partially fills the defect with structurally weak tissue that also exhibits limited durability.

Other procedural options such as periosteal grafting, osteochondral autografts and allografts, and autogenous chondrocyte cell implantation have been used to repair cartilage defects for the purpose of reducing pain and restoring function. The success of these procedures generally diminishes over time, possibly due to formation of fibrocartilage, inadequate development of repair tissue, poor cell differentiation, and/or poor bonding to the surrounding articular cartilage borders. Intact full thickness grafts, such as osteochondral autografts and allografts, also may suffer from mismatched sizes, immunologic rejection, and poor adhesion of cartilage to bony surfaces. For autogenous chondrocyte cell implantation, two surgeries are required: chondrocytes are first obtained from an uninvolved area of cartilage and cultured for 14 to 21 days, then the cultured cells are injected into the defect exposed via an open incision and covered with a periosteal flap excised from the proximal medial tibia.

Various methods of promoting tissue growth and repair, and in particular cartilage repair, have been suggested and include the use of tissue particles derived from grinding nondemineralized, articular cartilage into pieces of about 60 µm to about 500 µm (Malinin U.S. Patent Application No. 20050196460); mincing tissue into particles using two parallel blades, resulting in particles of about 0.1 to about 3 mm$^3$ in size and containing at least one viable cell (Binette et al. U.S. Patent Application No. 20040078090); pulverizing soft tissue into morsels of about 1 to about 100 µm that may then be combined with viable elements (cells) and/or bioactive molecules (Awad et al. U.S. Patent Application No. 20050288796); and, milling allograft cartilage, which is then lyophilized to create particles in the size of about 0.01 mm to about 1 mm that can be formulated into a paste (Gomes et al. U.S. Patent Application No. 20040219182). Various methods of tissue preparation have also been disclosed including a method of generating dermal tissue pieces of about 50 µm to about 1500 µm using a roller with multiple blades (Mishra et al. U.S. Patent Application No. 20040175690).

Cell and/or tissue viability for implants needs to be improved. For example, homogenizers used to generate tissue particles have resulted in about 5% of the cells remaining viable following homogenization. Enzymatic digestion, which is often used to generate cells for autogenous chondrocyte cell transplantation, results in poor cell viability following initial isolation.

Improved compositions and methods for repairing tissue defects and in particular, articular cartilage defects are desired.

SUMMARY OF THE INVENTION

One embodiment is a composition including isolated small tissue particles composed of cells and their associated extracellular molecules (e.g., proteins, polysaccharides, proteoglycans, etc.) known as the extracellular matrix (ECM). The tissue particles are sized such that in some embodiments, the particles have at least one dimension less than about 60 µm. In another embodiment, the particles have at least one dimension less than about 1 mm. In another embodiment, the particles are sized so that the volume is less than about 1 mm$^3$. In some embodiments, at least about 50% of the cells in the tissue particles are viable. In other embodiments, at least about 80% of the cells in the tissue particles are viable. In some embodiments, the composition may also contain additives such as adhesives, solutions, and bioactive agents. Examples of adhesives include fibrin glue, Tisseal (Baxter BioScience, Deerfield Ill.), and Surgicel (Johnson & Johnson, New Brunswick N.J.). Examples of bioactive agents include fibrinogen, thrombin, bone morphogenic proteins (BMP), insulin-like growth factors (IGF), transforming growth factors (TGF) including the beta form (TGFβ), platelet-derived growth factor (PDGF), and bone marrow aspirate.

Another embodiment is a method for creating small tissue particles whereby a tissue sample is positioned on a cutting device containing at least two blades in parallel in one embodiment, and at least three blades in parallel in another embodiment. In embodiments containing at least three blades, spacing between the blades may be uniform or may vary. The space between the blades may define a dimension of the particle. In one embodiment, at least one blade is curved. In another embodiment, at least two blades are not parallel. In one embodiment, the sizing apparatus comprises three blades mounted in parallel and separated by spacers having a width of about 60 µm. By changing the relative spatial relationship between the tissue sample and the cutting apparatus, cuts can be made in the horizontal, vertical, and coronal planes. Because the angle between these planes can be varied, the resulting tissue particle can be sized to a variety of shapes, including cubes, triangles, quadrilaterals, and other polygons.

Another embodiment is a method using the described compositions in ameliorating a tissue defect. In one embodiment, the defective tissue may be cartilage, bone, ligament, meniscus, tendon, muscle, nucleus pulposus, gingiva, annulus fibrosus, periosteum, perichondrium, fascia, and/or perineurium. In one embodiment, defects within articular cartilage are subjected to the method. In general, the method includes placing the isolated sized tissue particles into a tissue defect site. Retention of the tissue particles in the defect site is facilitated by the small particle size. In certain embodiments, retention of the tissue particles at the defect site may be enhanced by techniques such as microfracture and use of adhesives.

Another embodiment is a use of the inventive small tissue particles under cell culture conditions and, for example, as part of in vitro experimentation and/or to propagate cells in culture.

The method and composition will be further appreciated with reference to the following figures and description.

BRIEF DESCRIPTION OF THE DRAWINGS

This application contains at least one drawing executed in color. A Petition under 37 C.F.R. §1.84 requesting acceptance of the color drawings is filed separately on even date herewith. Copies of this patent or patent application publication with color drawing(s) will be provided by the Office upon request and payment of the necessary fee.

DETAILED DESCRIPTION

In one embodiment, a composition comprising a plurality of isolated tissue particles is disclosed. The particles comprise cells and their associated extracellular molecules, (e.g. proteins, polysaccharides, proteoglycans, etc.), which collectively are termed a matrix. In another embodiment, the tissue particles are comprised of cells wherein at least about 50% of the cells are viable. In another embodiment, the tissue particles are comprised of cells wherein at least about 60% of the cells are viable. In another embodiment, the tissue particles are comprised of cells wherein at least about 65% of the cells are viable.

Figure 1A:
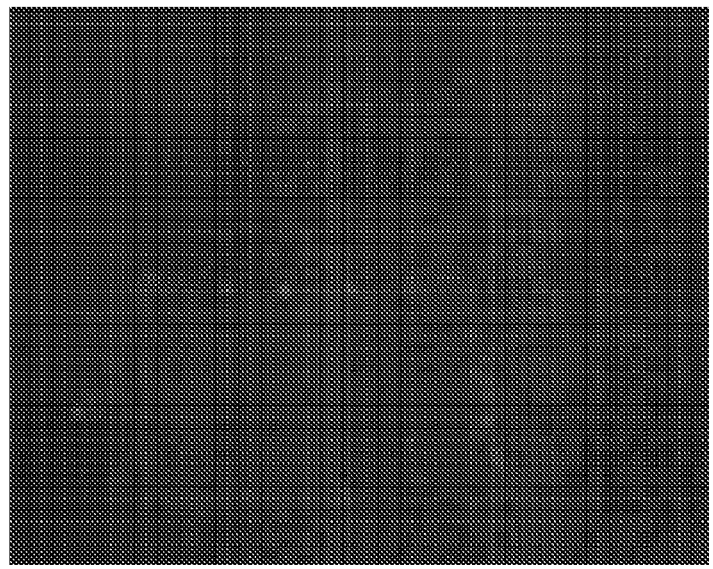
FIG. 1A is a photograph of particles with only live cell staining.
Figure 1B:
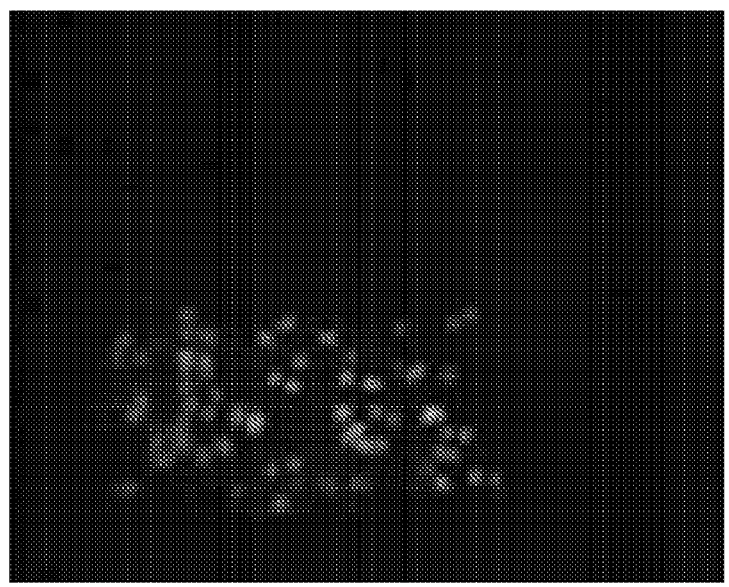
FIG. 1B is a photograph of particles with only dead cell staining.

In another embodiment, the tissue particles are comprised of cells wherein at least about 70% of the cells are viable. In another embodiment, the tissue particles are comprised of cells wherein at least about 75% of the cells are viable. In another embodiment, the tissue particles are comprised of cells wherein at least about 80% of the cells are viable. Cell viability indicates that the cell is alive and able to perform one or more intrinsic biological functions (e.g., cellular signaling, maintenance of cellular homeostasis, etc.), and also may include cells that are dormant or arrested in a stage of the cell cycle. Cells that are not viable are cells that are dead. The absolute number of viable cells may vary depending on, for example, the tissue type used to make the particles and/or particle size. The presence of viable cells in the tissue particle composition facilitates use of the composition in ameliorating tissue defects, as described more fully below. For example, viable cells provide stimulators and/or cues for tissue remodeling, growth, and/or repair. Methods to measure cell viability are known to one skilled in the art and include facilitated dyes and biochemical assays. For example, cell viability in the tissue particles was measured using the LIVE/DEAD® viability assay (Invitrogen, Eugene Oreg.) where the calcein dye is retained in live cells and emits a green fluorescence and the ethidium homodimer is able to enter cells with damaged membrane and emits red fluorescence when interacting with nucleic acids. FIG. 1A shows dead cells that emit red fluorescence in tissue particles in one embodiment of the invention. FIG. 1B shows living cells that emit green fluorescence in tissue particles in one embodiment of the invention. The results in FIGS. 1A and 1B showed satisfactory uptake of the dyes in to the small tissue particles.

Along with cells, the tissue particles also contain extracellular molecules, often referred to as the extracellular matrix (ECM). The ECM surrounds and supports cells within mammalian tissues, and is composed of three major classes of biomolecules: (i) structural proteins such as collagen and elastin; (ii) specialized proteins such as fibrillin, fibronectin, and laminin; and (iii) proteoglycans. Proteoglycans are composed of a protein core that is attached to long chains of repeating disaccharide units termed glycosaminoglycans (GAGs) and form complex high molecular weight components of the ECM. The ECM has many roles including cellular organization, guidance of cell migration and growth, and structure; the prominence of these roles can vary depending on the tissue. For example, the ECM plays an important role in force transmission and tissue structure maintenance especially in cartilage, tendons, ligaments, bone, and muscle. The precise composition of the ECM in the particles depends on factors such as the tissue from which the particles are obtained and any treatments or modifications thereof. Thus, the composition of the ECM will vary depending on the endogenous composition for that tissue type. Along with variations in ECM composition based on tissue type, the ECM may also be modified. As one example, the particles may be treated with bioactive proteins, such as BMP, IGF, TGF, PDGF, bone marrow aspirate, etc., to enhance the tissue repair ability of the particles. Also, the particles may be treated with enzymes that hydrolyze protein and/or glycans, such as trypsin and hyaluronidase, to increase the accessability of the ECM.

The size of the tissue particles of the inventive composition may vary depending on such factors as the type of source tissue used, the age of the tissue, and the intended subsequent use of the composition. In one embodiment, tissue particles are sized such that at least one dimension of the particle is less than 1 mm. In another embodiment, the tissue particles are sized such that at least one dimension is less than 60 μm. In another embodiment, the tissue particles are sized such that the particle is substantially cubical with each side about 60 μm or less. In another embodiment, the tissue is derived from a juvenile source and the tissue particles have a volume less than 1 mm$^3$. In another embodiment, the tissue particles have a volume of about $2\times10^{-4}$ mm$^3$. The tissue particles may be any shape, including but not limited to cubes and elongated strips. Sizing refers to cutting of the tissue sample into the desired size and/or shape, and is further described below.

The tissue particles may be derived from a variety of tissue types and tissue sources. The tissue may be autogenic, allogenic, or xenogenic with respect to the recipient of the inventive composition, as explained below. Any tissue is potentially suitable for use and tissue types may include cartilage, bone, ligament, meniscus, tendon, muscle, nucleus pulposus, gingival, annulus fibrosus, periosteum, perichondrium, fascia, and/or perineurium. In one embodiment, the tissue is articular cartilage. In another embodiment, the articular cartilage is hyaline cartilage and/or fibrocartilage.

In one embodiment, the tissue is engineered tissue. Engineering of the tissue refers to altering the physiology of the tissue such that it possesses traits that it would normally not have, magnifying and/or muting the existing tissue traits, and/or growing tissue in vitro. Engineered tissue may include tissue derived from a transgenic donor. Transgenic donor refers to tissue sources, such as animals, in which exogenous genetic material has been incorporated into the genome of the source. The incorporated genetic material may provide for the expression of a non-endogenous gene or may alter the expression levels of an endogenous gene. In another embodiment, the donor tissue may be genetically altered following removal from the donor. Examples of alterations of the tissue following excision and prior to or concomitant with culturing include alterations brought about by introduction of genetic material and/or bioactive agents. In the case of genetic manipulation, the tissue may be treated with genetic vectors using various methods of genetic introduction, e.g. viral- and lipid-mediated, as known in the art, to bring about alterations in endogenous or exogenous gene expression. Bioactive agents, such as growth factors, may be incubated with the cultured tissue to bring about alterations in tissue physiology. Engineered tissue may also refer to tissue that has been propagated or grown in vitro. Tissue grown in vitro refers to the creation and/or propagation of tissue outside an animal host. For example, in vitro grown tissue may result from tissue culture manipulations where cells are, for example, stimulated to form a tissue in an incubating vessel. Methods for producing in vitro tissue are known to one skilled in the art.

The developmental or maturation stage of the tissue used in the invention may also vary. For example, the tissue particles may be derived from embryonic, fetal, neonatal, juvenile, or adult tissue. In an embodiment where juvenile tissue is used, juvenile is defined as being less than 12 years old in the case of humans. Further, the tissue may be acutely isolated or cultured prior to sizing into particles. In the case of cultured tissue samples, the tissue is maintained in an environment that preserves the viability of the cells in the tissue. However, it is also understood by one skilled in the art that some cell death may occur as a result of in vitro tissue culturing. The tissue, either in preparation of culturing or following acute isolation, may be sized into smaller pieces that either facilitate subsequent sizing, e.g. results in a size that is easier to manipulate in the subsequent creation of tissue particles, or promotes cell viability in tissue culture, e.g. increases the surface area of the tissue and thus oxygen and nutrient accessibility to the cells. In another embodiment, the tissue is sized to the desired particle size prior to culture.

The composition may also include additional components. In one embodiment, the tissue particles of the composition are maintained or suspended in a solution. The solution may be a buffer that maintains the solution pH in a desired range. For example, the buffer may maintain the tissue particles in a solution in the range from about pH 6.8 to about pH 7.5. In other embodiments, the buffer may maintain the pH in the range of about pH 5 to about pH 7. The buffer, and the resulting buffering pH range chosen, depends on factors known to one skilled in the art including the tissue type and the effects of certain pH on that tissue type.

In another embodiment, the composition include bioactive agents. The bioactive agents may be either residual from culturing of the tissue sample as described above or may be added to the tissue particles at another time. Examples of bioactive agents include but are not limited to growth factors, hormones, and nutrients.

The inventive composition may also comprise an adhesive that aids in the attachment of the tissue particles to the site of tissue defect. The adhesive may be a naturally occurring bioadhesive such as fibrin. Thrombin converts soluble plasma fibrinogen into molecules of fibrin that polymerize and form a fibrin clot. Fibrin may encapsulate and/or enmesh the tissue particles at the sites of tissue defect. It should also be noted, however, that due to the small size of the inventive tissue particles, the particles are intrinsically adhesive to the site of tissue defect. In another embodiment, the tissue particles may be treated such that they become positively charged. The tissue particle may be charged by a variety of treatments including exposing the particles to an ionic detergent or a magnetic field, resulting in the creation of an overall positive charge on the particles. The overall positive charge of the particle facilitates adhesion of the particle to the predominantly negatively charged tissue defect. Increased adhesion of the particles to the tissue defect site may reduce the time required for tissue defect repair.

Figure 2:
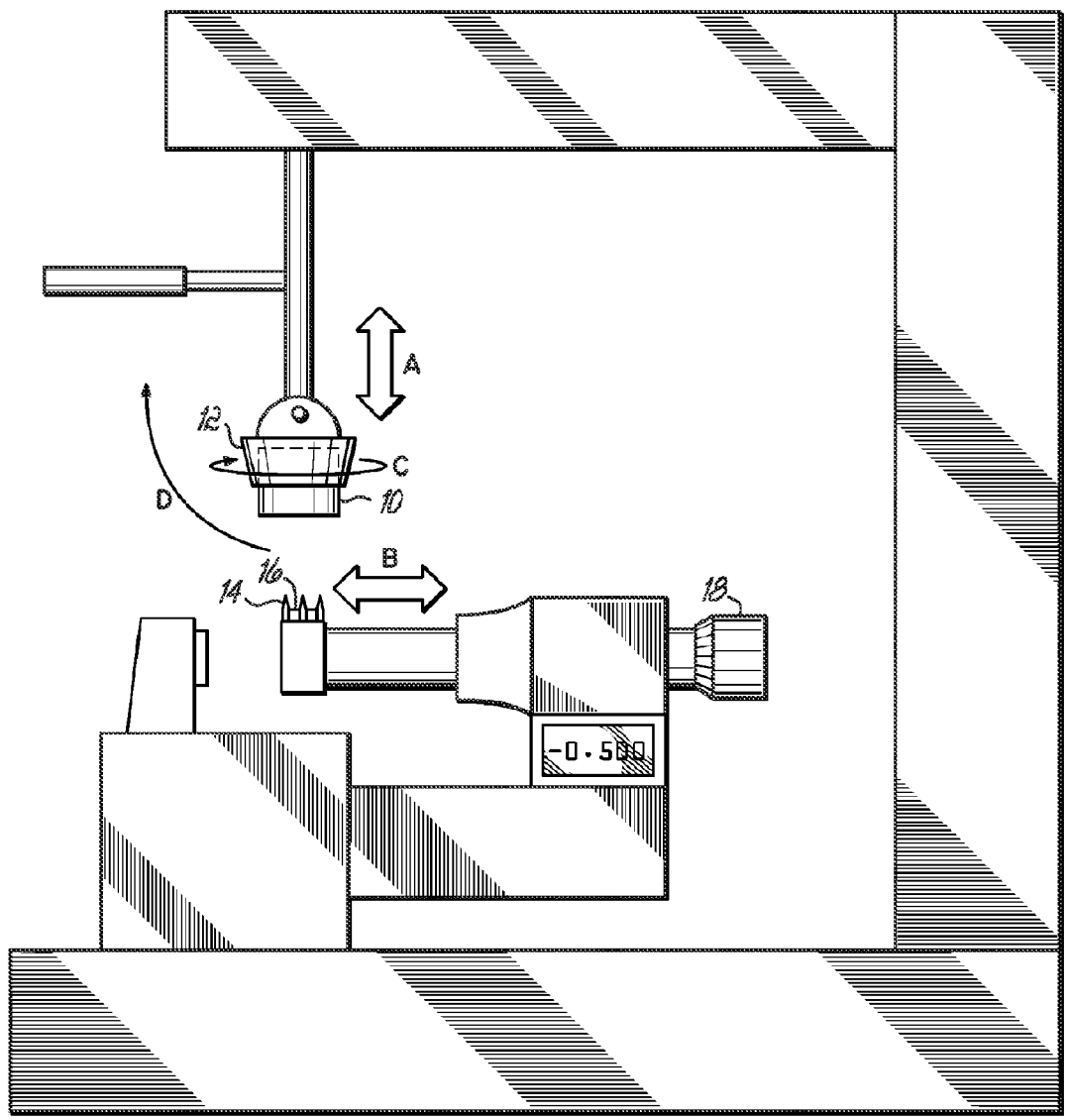
FIG. 2 shows an apparatus for sizing tissue particles.

In one embodiment, a method of preparing a composition comprising tissue sized into particles is disclosed. The tissue sample is initially cut into smaller pieces to facilitate subsequent sizing into tissue particles, e.g., using surgical tools known to one skilled in the art, such as a scalpel. In one embodiment, the tissue is initially cut into pieces of about 5 mm to about 11 mm. In another embodiment, the tissue, which may have been cultured, has already been subjected to the initial cutting process and is of the approximate size for subsequent sizing. As shown in the schematic of FIG. 2 (not to scale), once the tissue 10 is of the appropriate initial size, it is mounted on a jaw 12 of an axial cylinder. By extending the axial cylinder along axis A, the tissue 10 contacts the blades 14 mounted in opposition of the jaw. In one embodiment, the tissue is contacted with at least two blades mounted in parallel on a substantially flat surface. In another embodiment, the tissue is contacted with three blades mounted in parallel on a substantially flat surface. In another embodiment, the blades 14 are not parallel to each other and may also include blades that are not straight, e.g., curved. The configuration of blades 14 will also include spacers 16 between the blades, the width of which will correspond to the desired dimension between parallel cuts. In certain embodiments, the spacers 16 between the blades 14 will be the same size and in other embodiments, the spacers 16 may be of different sizes. The blades will be sufficiently sharp so that damage and/or loss of the tissue will be minimized.

Figure 3A:
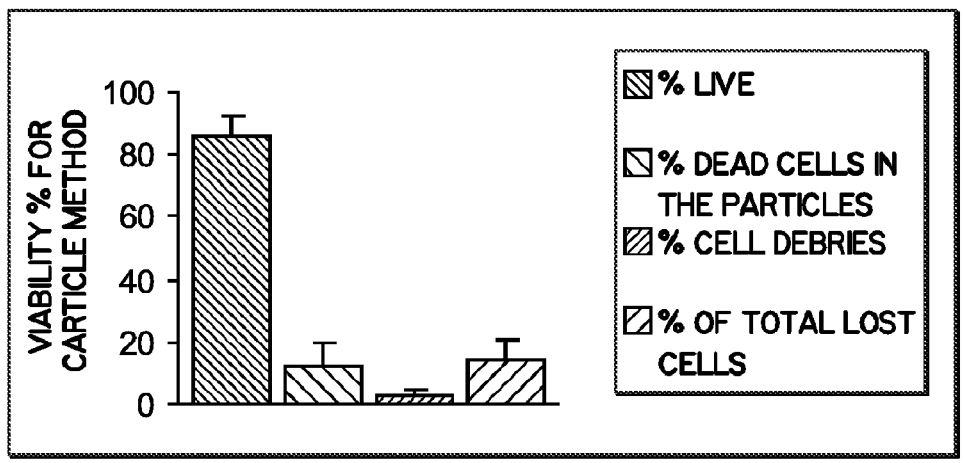
FIG. 3A shows the percentage of viable cells following one embodiment of the method.
Figure 3B:
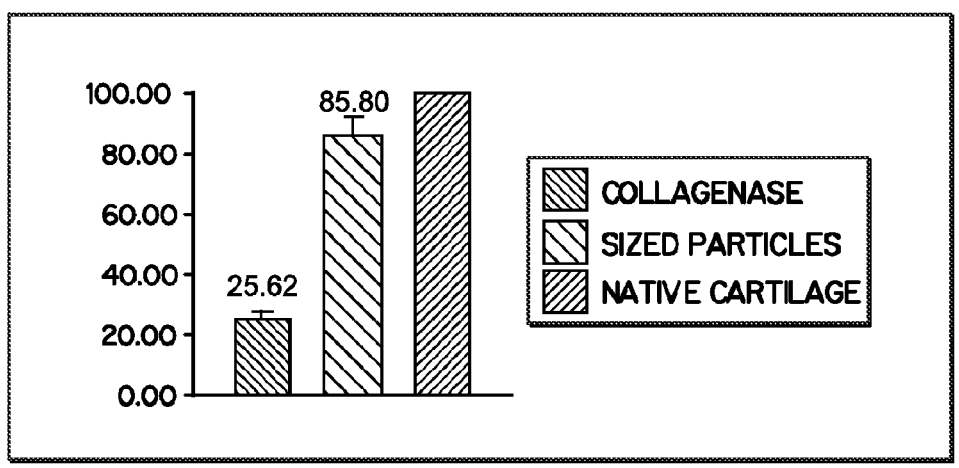
FIG. 3B shows the percentage of viable cells following enzymatic digestion versus an embodiment of the invention.

The method may be conducted in the absence of exogenously added digestive enzymes. Although digestive enzymes promote cell dissociation, they also may decrease the percent of viable cells resulting from the treatment. In FIG. 3, the viability of cells following one embodiment of the inventive method, as determined by LIVE/DEAD® viability assay, was about 85% (FIG. 3A) while viability of cells following enzymatic treatment with collagenase resulted in about 25% viable cells (FIG. 3B). Without being held to a single theory, it is believed that the digestive enzyme damages the cell membrane components, contributing to the death of the cell.

Figure 4:
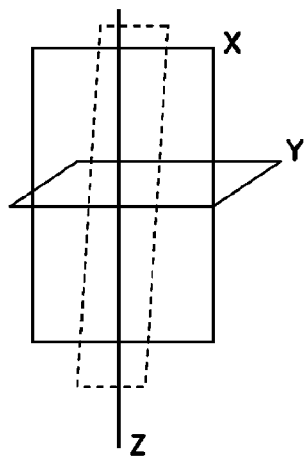
FIG. 4 shows a schematic representation of the three particle planes defined by the x-axis, y-axis, and z-axis.

The first contact between the blades and the tissue results in parallel cuts in, for example, the x-axis plane of the tissue sample, as shown in FIG. 4. In different embodiments, the tissue may be pushed against the blades or alternatively the blades may be pushed against the tissue. In another embodiment, the blade and tissue sample are both moved towards each other. In certain embodiments, the blades may not be parallel and therefore, would not result in parallel cuts. However, for simplicity, the inventive method will be described in terms of parallel blades making parallel cuts but in all cases, the blades and resulting cuts may not be parallel, and also may be non-straight, e.g., curved. Following the first contact between the blades and the tissue, the sample and/or blades can then be translationally moved along axis B, e.g. without rotation, so that further cuts can be made in parallel with the previous cuts and still in the same plane. In one embodiment, the blades are translationally moved with precision of about 1 μm using a digital micrometer 18, as shown in FIG. 2. The blades and/or tissue sample is then rotated relative to one another in rotation C about axis A, defining a second orientation and the blades and tissue are again caused to contact, making cuts in, for example, the y-axis plane, as shown in FIG. 4. In this second orientation, the blades and/or tissue can again be translationally moved so that a series of parallel cuts can be made. In one embodiment, the second contact between the blades and tissue results in substantially perpendicular cuts in the tissue wherein the angle between the first and second cut is about 90°. However, the angle between the first and second cuts may range from about 1° to about 179°. In one embodiment, the blades and/or the tissue sample are moved to achieve a third orientation wherein the blades cut the tissue sample in, for example, the z-axis plane plane, as shown in FIG. 4. The third orientation can be achieved by moving the tissue in direction D, as shown in FIG. 2. In one embodiment, the plane defined by this third orientation cuts the tissue substantially perpendicular to the plane of either the first or second cut, for example, the x-axis or y-axis plane, and results in a particle that is substantially cubicle. However, the angle between the third and either of the first or second cutting planes may range from about 1° to about 179°. Thus, by choosing the angles between the cut planes, the geometry of the resultant tissue particle can be varied.

Tissue particles of various sizes can be made by varying the size of the spacers between the blades and the angle between the cuts. In one embodiment, the tissue is cut using the procedure described above wherein three blades contact the tissue, the resultant tissue particle is sized such that at least one dimension is less than 60 μm. In another embodiment, the tissue is cut using the procedure described above wherein three blades contact the tissue and the tissue is derived from a juvenile, non-dermal source, the resultant tissue particle is sized such that at least one dimension is less than 1 mm. In another embodiment, the resultant tissue particle size is less than 1 mm$^3$. The method produces tissue particles of the desired dimensions and also maintained a high percentage, e.g. above about 85%, viable cells (See FIG. 3A).

As described above, the tissue source used by the inventive method to generate tissue particles may be used from any source and with any type of tissue including autogenic, allogenic, xenogenic, cultured, and engineered tissue and of any maturation stage.

In one embodiment, a method of ameliorating a damaged tissue in a mammal is disclosed. The tissue particle composition is introduced into or in proximity to a damaged tissue under conditions sufficient to ameliorate the damaged tissue. The composition may include a plurality of tissue particles sized from tissue. In addition, the particles may include both cells and extracellular molecules organized in a matrix, as described above. In one embodiment, the damaged tissue may be articular cartilage. In the case of damaged articular cartilage, the cartilage lesion may be debrided back to a stable base cartilage and loose or fibrillated cartilage may be resected. In one embodiment, in the case of articular cartilage, the subchondral base is microfractured until bleeding occurs from the subchondral bone. Microfracture entails creating a series of small fractures in the bone of about 3 mm to about 4 mm in depth using an awl. Alternatively, a drill may be used to create holes in the subchondral bone, with care to not cause heat necrosis in the site. The composition is applied into the area of and/or proximate the defect.

Figure 5A:
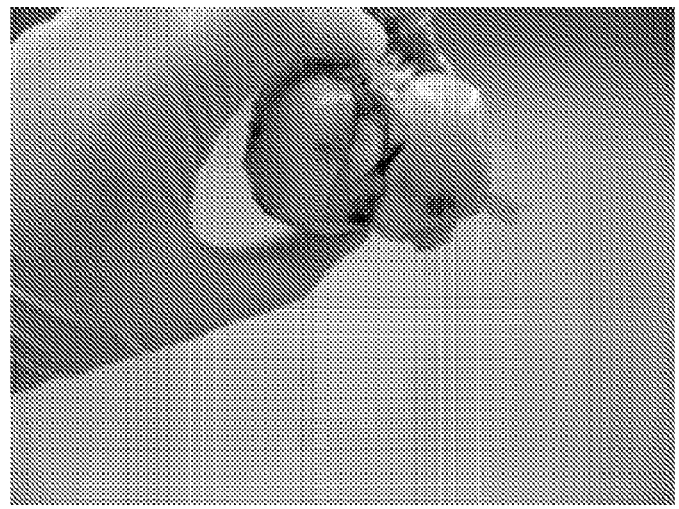
FIG. 5A shows a surface of a porcine knee joint that has been subjected to one embodiment of the invention.
Figure 5B:
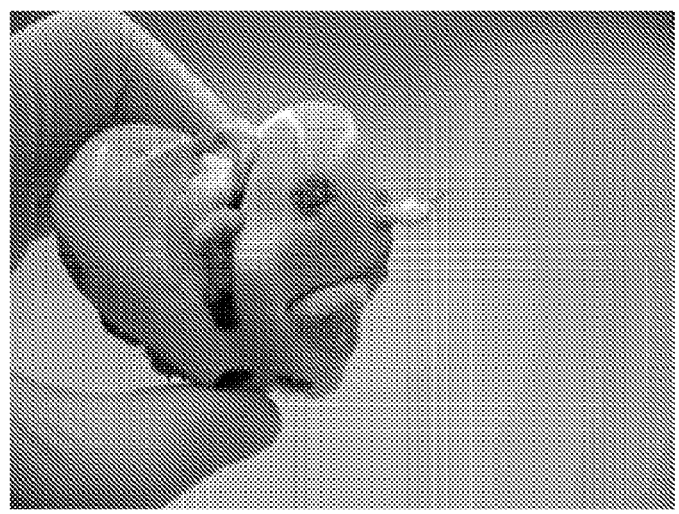
FIG. 5B shows a surface of a porcine knee joint that has been subjected to another embodiment of the invention.

In one embodiment, the method of ameliorating damaged tissue also includes adhering the inventive composition to the damaged tissue. If the method is conducted in conjunction with microfracture, adhesive properties of bleeding bone secure the tissue particles in place, as shown in FIG. 5A. Specifically, the resulting blood clot from the bleeding bone serves as a biological glue that maintains the particles on the surface near the defect. Also, due to the small size of the tissue particles, the particles naturally remain in the defect, as shown in FIG. 5B, possibly as a result of surface tension. The inventive composition may also include adhesives such as fibrin, hyaluronic acid, fibrin glue, fibrin clot, collagen gel, alginate gel, gelatin-resorcin-formalin adhesive, mussel-based adhesive, dihydroxyphenylalanine (DOPA) based adhesive, chitosan, transglutaminase, poly(amino acid)-based adhesive, cellulose-based adhesive, polysaccharide-based adhesive, synthetic acrylate-based adhesives, platelet rich plasma (PRP), platelet poor plasma (PPP), clot of PRP, clot of PPP, MATRIGEL® (BD Biosciences, San Jose Calif.), monostearoyl glycerol co-succinate (MGSA), monostearoyl glycerol co-succinate/polyethylene glycol (MGSA/PEG) copolymers, laminin, elastin, proteoglycans, and combinations thereof.

In one embodiment, the tissue particles of the inventive composition may have been treated such that the particles exhibit a net charge, as described above, that facilitates electrostatic adhesion to the tissue defect. Other techniques known to one skilled in the art, such as flaps, may also be used to keep the particles in the defect site.

In one embodiment, the method is conducted using a minimally invasive procedure, e.g. arthroscopy. The use of a minimally invasive procedure allows a smaller incision, resulting in less pain, a shorter in-patient stay, and a faster recovery time than traditional more invasive procedures. The use of a minimally invasive procedure such as arthroscopy may also aid in diminishing potential post-operative complications such as soft tissue fibrosis.

In one embodiment, the damaged tissue may be orthopedic tissue such as cartilage, bone, ligament, meniscus, tendon, and/or other muscle. In another embodiment, the damaged tissue may be nucleus pulposus, gingival, annulus fibrosus, periosteum, perichondrium, fascia, and/or perineurium. In one embodiment, the damaged tissue and the tissue that is used as the source for the inventive composition are the same tissue type, e.g. articular cartilage. In another embodiment, the damaged tissue and the tissue that is used as the source for the inventive composition are different tissue types, including autogenic, allogenic, xenogenic, cultured, engineered tissue, and of any maturation stage.

One embodiment discloses a biocompatible implantable composition comprising a plurality of biological tissue particles sized from tissue derived from viable juvenile cartilage, wherein the particles are comprised of chondrocytes having at least about 80% viability and extrachrondrocyte proteins, each particle less than 60 µm, and the composition is capable of implantation in a mammal.

In one embodiment, particulate cartilage compositions are created and used for cartilage regeneration by stimulating chondrogenesis. Articular cartilage may be obtained from the articular surfaces of joints, such as from distal femurs, proximal tibia, acetabul, heads of femurs, and/or heads of radii, as well as from other sites where hyaline cartilage is present, e.g., auricular, nasal, temporomandibular joint, and costal margin. The cartilage may be removed, for example, with a scalpel blade, rongeur, or other surgical instrument. In one embodiment, cartilage is removed down to subchondral bone, without removing bone. The articular cartilage may include articular hyaline cartilage and/or fibrocartilage and may comprise allogeneic and/or xenogeneic cartilage.

The following example further illustrates embodiments of the invention.

EXAMPLE

Cartilage tissue particles were assessed for cell viability and evaluation in cartilage defect repair. All procedures were conducted in compliance with relevant regulations for the use of animal tissue. Porcine knee joints were obtained from a local abattoir. A knee joint was opened using a scalpel and the articular cartilage from the condyle load bearing area was exposed. Using a 7.5 mm diameter coring reamer, an osteochondral plug was obtained.

The osteochondral plug was mounted on the jaw of the cutting device (FIG. 2) and a series of cuts were made using three multiple blades to obtain viable small tissue particles.

Tissue particles were stained using LIVE/DEAD® stain to determine cell viability. The LIVE/DEAD® stain uses a membrane-permeant CALCEIN AM that is cleaved by endogenous esterases in the live cells to yield cytoplasmic green fluorescence, and the membrane-impermeant ethidium homodimer-1 labels nucleic acids of membrane-compromised cells, e.g. dead cells, with red fluorescence. Pictures of the stained slides were analyzed using NIH imaging software and the number of total and viable cells was calculated. For the enzymatic digestion method, cartilage was shaved off the articular surface and collected in a Petri dish. Tissue weight was recorded. The cartilage tissue blocks were digested in a 1:10 mass:volume ratio in 0.15% of collagenase type II for about 12-16 hours until no visible fragments remained. The cell-collagenase solution was filtered and washed with phosphate-buffered saline. Isolated cells were counted and viability was determined using LIVE/DEAD® staining. The number of viable cells was normalized to the tissue weight and represented as a percentage of the absolute number of cells in a given unit of tissue, as shown in FIG. 3A. Paired t-test statistical analysis was performed using Sigma Stat 2.0 software.

Results showed that tissue particles had a regular geometry. The majority of the particles were from 50 microns to 240 microns. LIVE/DEAD® staining experiments showed good tissue penetration of the dyes due to the size of the particles. Although a small percentage, about 10% to about 15%, of the tissue was lost during the cutting procedure, cell viability in the tissue particles was significantly higher than the percentage of viable cells obtained by digestion method (Compare FIGS. 3A and 3B). Tissue particles seeded on the surface of the joint remained attached to the surface against gravity for an indefinite period of time as long as conditions were maintained (FIG. 5B) and the adhesion was increased when microfracture was simulated by compressing the subchondral bone and causing to bleed (FIG. 5A).

The above results showed that small tissue living particles were obtained from an autologous source. The results also showed that cell viability inside of the particle remained higher than 85%.

It should be understood that the embodiments and examples described are only illustrative and are not limiting in any way. Therefore, various changes, modifications or alterations to these embodiments may be made or resorted to without departing from the spirit of the invention and the scope of the following claims.

What is claimed is:

1. A composition comprising:
    a plurality of isolated allogenic human juvenile cartilage particles, the cartilage particles including chondrocytes, at least about 50% of which are viable, and chondrocyte-associated extracellular biomolecules, each cartilage particle having at least one dimension less than 1 mm; and
    a cartilage particle maintenance solution.

2. The composition of claim 1, wherein the cartilage particles are obtained from a juvenile donor less than 12 years of age.

3. The composition of claim 1, wherein the cartilage particles comprise articular cartilage.

4. The composition of claim 1, wherein the percentage of viable chondrocytes is selected from at least about 60%, at least about 65%, at least about 70%, at least about 75% and at least about 80%.

5. The composition of claim 4, wherein the percentage of viable chondrocytes is at least about 75%.

6. The composition of claim 1, wherein the percentage of viable chondrocytes is determined by a membrane permeability assay.

7. The composition of claim 6, wherein the membrane permeability assay includes fluorescent labeling of nucleic acids.

8. The composition of claim 1, wherein the chondrocyte-associated extracellular biomolecules are selected from proteins, polysaccharides, proteoglycans and combinations thereof.

9. The composition of claim 8, wherein the chondrocyte-associated extracellular biomolecules are combinations of proteins, polysaccharides and proteoglycans.

10. The composition of claim 1, wherein the cartilage particles have a volume less than 1 $mm^3$.

11. The composition of claim 10, wherein the cartilage particles have a volume of about $2 \times 10^{-4}$ $mm^3$.

12. The composition of claim 1, wherein the maintenance solution comprises a buffer.

13. The composition of claim 12, wherein the buffer maintains the solution pH between about 5 and about 7.

14. The composition of claim 13, wherein the buffer maintains the solution pH between about 6.8 and about 7.5.

15. The composition of claim 1, further comprising at least one bioactive agent.

16. The composition of claim 15, wherein the at least one bioactive agent is selected from a growth factor, a hormone, a nutrient and combinations thereof.

17. The composition of claim 16, wherein the growth factor is selected from a BMP, an IGF, a TGF, a PDGF and combinations thereof.

18. The composition of claim 17, wherein the growth factor is a TGF.

19. The composition of claim 1, further comprising an adhesive.

20. The composition of claim 19, wherein the adhesive is selected from fibrin, hyaluronic acid, fibrin glue, fibrin clot, collagen gel, alginate gel, gelatin-resorcin-formalin adhesive, mussel-based adhesive, dihydroxyphenylalanine (DOPA) based adhesive, chitosan, transglutaminase, poly(amino acid)-based adhesive, cellulose-based adhesive, polysaccharide-based adhesive, synthetic acrylate-based adhesives, platelet rich plasma (PRP), platelet poor plasma (PPP), clot of PRP, clot of PPP, solubilized basement membrane (MATRIGEL®), monostearoyl glycerol co-succinate (MGSA), monostearoyl glycerol co-succinate/polyethylene glycol (MGSA/PEG) copolymers, laminin, elastin, proteoglycans, and combinations thereof.

21. The composition of claim 20, wherein the adhesive includes fibrin.

* * * * *